US008175707B1

(12) United States Patent
Wright et al.

(10) Patent No.: US 8,175,707 B1
(45) Date of Patent: May 8, 2012

(54) ENHANCEMENT OF RATE RESPONSIVE IEGM-BASED AV/PV AND VV DELAY ALGORITHMS

(75) Inventors: Connie Wright, San Diego, CA (US); Xiaoyi Min, Thousand Oaks, CA (US); Euljoon Park, Valencia, CA (US); Scott Simon, Billings, MT (US)

(73) Assignee: Pacesetter, Inc., Sylmar, CA (US)

( * ) Notice: Subject to any disclaimer, the term of this patent is extended or adjusted under 35 U.S.C. 154(b) by 334 days.

(21) Appl. No.: 11/951,928

(22) Filed: Dec. 6, 2007

(51) Int. Cl.
*A61N 1/365* (2006.01)

(52) U.S. Cl. .............................................. 607/18; 607/9

(58) Field of Classification Search .................. 607/4, 5, 607/9, 16, 17, 18, 25, 115–123; 600/547
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,466,254 A | 11/1995 | Helland | |
| 5,476,483 A | 12/1995 | Bornzin et al. | |
| 7,181,284 B2 * | 2/2007 | Burnes et al. | 607/25 |
| 7,187,972 B1 * | 3/2007 | Fain et al. | 607/14 |
| 7,546,161 B1 * | 6/2009 | Bjorling et al. | 607/28 |
| 2005/0137630 A1 * | 6/2005 | Ding et al. | 607/9 |
| 2005/0137631 A1 * | 6/2005 | Yu et al. | 607/9 |
| 2005/0256545 A1 * | 11/2005 | Koh et al. | 607/17 |

OTHER PUBLICATIONS

Giannuzzi, Pantaleo et al., "Attenuation of Unfavorable Remodeling by Exercise Training in Postinfarction Patients with Left Ventricular Dysfunction," Circulation. 1997;96:1790-1797.
Ismer, B. et al., "Exercise Induced Sympathetic Influences Do Not Change Interatrial Conduction Times in VDD and DDD Pacing," PACE 1996;19[Pt. II]:1786-1790.
Kass, David A. et al., "Improved Left Ventricular Mechanics From Acute VDD Pacing in Patients With Dilated Cardiomyopathy and Ventricular Conduction Delay," Circulation. 1999;99:1567-1573.
Morales, Maria-Aurora et al., "Atrioventricular Delay Optimization by Doppler-Derived Left Ventricular dP/dt Improves 6-Month Outcome of Resynchronized Patients," PACE 2006;29:564-568.

* cited by examiner

*Primary Examiner* — Carl H Layno
*Assistant Examiner* — Pamela M Bays

(57) ABSTRACT

An exemplary method includes delivering a cardiac resynchronization therapy using an atrio-ventricular delay and an interventricular delay, monitoring patient activity, optimizing the atrio-ventricular delay and the interventricular delay for a plurality of patient activity states to generate a plurality of optimal atrio-ventricular delays and a plurality of optimal interventricular delays, storing the optimal atrio-ventricular delays and the optimal interventricular delays in association with corresponding patient activity states, detecting a change in patient activity, adjusting an atrial pacing rate in response to the detected change in patient activity based at least in part on a heart failure status and setting the atrio-ventricular delay and the interventricular delay, in response to the detected change in patient activity, using a stored optimal atrio-ventricular delay that corresponds to the patient activity and a stored optimal interventricular delay that corresponds to the patient activity. Other exemplary technologies are also disclosed.

18 Claims, 15 Drawing Sheets

SCHEME 410
Optimization Algorithm for PV/AV and VV
Implemented by Implantable Device
(E.G., Post-Implant During First 6 Months)

SCHEME 420
Optimization Algorithm for PV/AV and VV
Implemented by Implantable Device
Acquired in Conjunction with Patient Activity Information
(E.G., to Know How to Respond to Exercise)

SCHEME 430
Optimization Algorithm for PV/AV and VV
Implemented by Implantable Device
Responsive to Patient Activity
(E.G., Improved Response to Exercise)

SCHEME 440
Optimization Algorithm for Heart Rate
Implemented by Implantable Device
Responsive to Patient Activity
and Patient Heart Failure Status
(E.G., Improved Rate Response to Exercise to Improve QOL)

SCHEME 450
Optimization Algorithm for Heart Rate and PV/AV and VV
Implemented by Implantable Device
Responsive to Patient Activity
and Patient Heart Failure Status
(E.G., Improved CRT Response to Exercise to Improve QOL)

FIG. 4

PATIENT RATE ADJUSTMENT RESPONSIVE TO PATIENT ACTIVITY
500
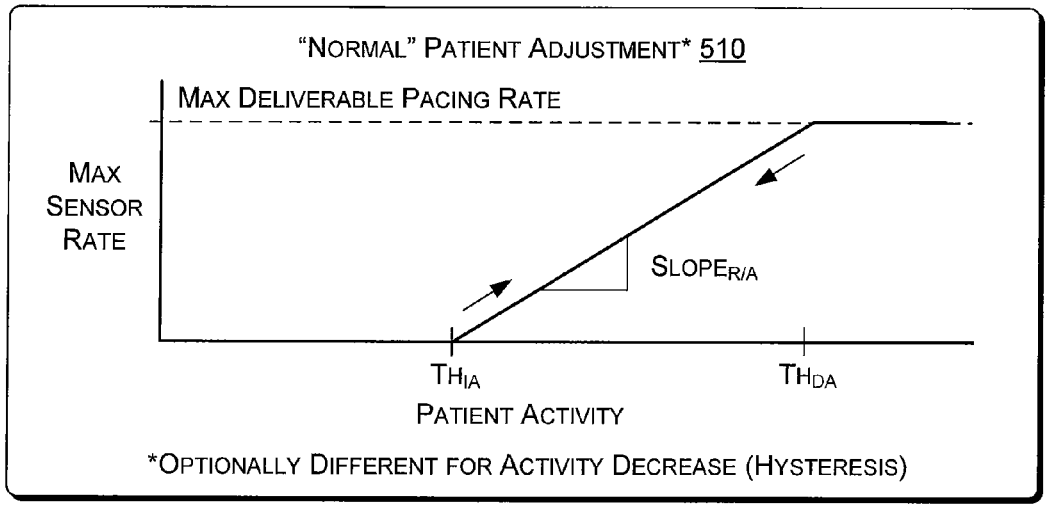
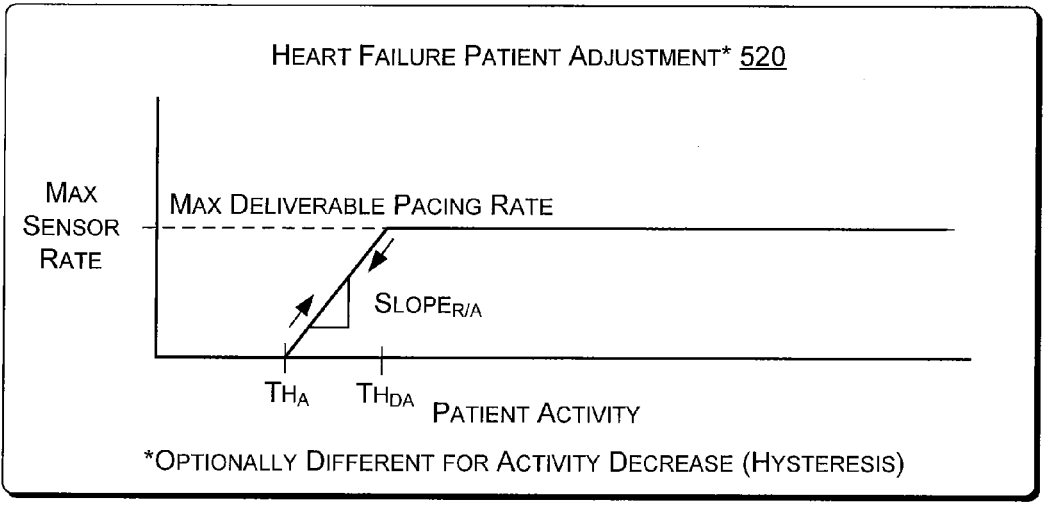
| PATIENT RATE ADJUSTMENT PARAMETERS 530 | | | |
|---|---|---|---|
| $TH_{IA}, TH_{DA}$ | NORMAL | > | HEART FAILURE |
| $SLOPE_{R/A}$ | NORMAL | < | HEART FAILURE |
| MAX DELIVERABLE RATE | NORMAL | > | HEART FAILURE |
FIG. 5

EXEMPLARY METHOD 1300

Exemplary Methods 1500

States 1510

$AS_0$ = Base State (e.g., Rest)
$AS_1$ = Active State 1
$AS_2$ = Active State 2
$AS_N$ = Active State N

PV or AV States 1520

$\beta = \delta/DD(AS_0)$
$\beta = \delta/AD(AS_0)$ $\delta = f(\Delta P(AS_0)) \quad \delta = f(\Delta A(AS_0))$
$\delta = f(\Delta P(AS_x)) \quad \delta = f(\Delta A(AS_x))$ $PV(AS_0) = \Delta P(AS_0) + \delta$
$AV(AS_0) = \Delta A(AS_0) + \delta$ $PV(AS_x) = \Delta P(AS_x) + \beta \cdot DD(AS_x)$
$AV(AS_x) = \Delta A(AS_x) + \beta \cdot AD(AS_x)$ $PV(AS_0) = \Delta P(AS_0) + \delta - PL$
$AV(AS_0) = \Delta A(AS_0) + \delta - PL$ $PV(AS_x) = \Delta P(AS_x) + \beta \cdot DD(AS_x) - PL$
$AV(AS_x) = \Delta A(AS_x) + \beta \cdot AD(AS_x) - PL$

VV States 1530

$\alpha$ = Constant
$\alpha = \alpha(AS_0)$
$\alpha = \alpha(AS_x)$ $\Delta(AS_0) = R_{LV}(AS_0) - R_{RV}(AS_0)$
$\Delta(AS_x) = R_{LV}(AS_x) - R_{RV}(AS_x)$ $\Delta_{IVCD}(AS_0) = IVCD\text{-}LR(AS_0) - IVCD\text{-}RL(AS_0)$
$\Delta_{IVCD}(AS_x) = IVCD\text{-}LR(AS_x) - IVCD\text{-}RL(AS_x)$ $VV(AS_0) = \alpha \ast (\Delta(AS_0) + \Delta_{IVCD}(AS_0))$
$VV(AS_x) = \alpha \ast (\Delta(AS_x) + \Delta_{IVCD}(AS_x))$ $VV(AS_0) = \alpha \ast (\Delta(AS_0) + \Delta_{IVCD}(AS_0)) - \Delta PL$
$VV(AS_x) = \alpha \ast (\Delta(AS_x) + \Delta_{IVCD}(AS_x)) - \Delta PL$

FIG. 15

ENHANCEMENT OF RATE RESPONSIVE IEGM-BASED AV/PV AND VV DELAY ALGORITHMS

RELATED APPLICATIONS

This application is related to U.S. patent application Ser. No. 11/610,162 now U.S. Pat. No. 7,778,706, filed on Dec. 13, 2006, entitled "Rate Adaptive Biventricular and Cardiac Resynchronization Therapy", which is incorporated by reference herein; and related to U.S. Pat. No. 7,248,925, issued Jul. 24, 2007, entitled "System and Method for Determining Optimal Atrioventricular Delay Based on Intrinsic Conduction Delays".

TECHNICAL FIELD

Exemplary technologies presented herein generally relate to cardiac pacing and/or stimulation therapy. Various techniques adjust pacing therapy based on patient activity.

BACKGROUND

Clinical studies related to cardiac pacing have shown that an optimal atrio-ventricular delay (e.g., AV delay) and/or an optimal interventricular delay (e.g., VV delay) can improve cardiac performance. However, such optimal delays depend on a variety of factors that may vary over time. Thus, what is "optimal" may vary over time. An optimization of AV delay and/or VV delay may occur at implantation and sometimes, a re-optimization may occur during a follow-up consultation. While such optimizations are beneficial, the benefits may not be long lasting due to changes in various factors related to device and/or cardiac function. As described herein, various exemplary methods, devices and/or systems aim to determine and/or adjust AV delay, VV delay and/or other interchamber delays.

SUMMARY

An exemplary method includes delivering a cardiac resynchronization therapy using an atrio-ventricular delay and an interventricular delay, monitoring patient activity, optimizing the atrio-ventricular delay and the interventricular delay for a plurality of patient activity states to generate a plurality of optimal atrio-ventricular delays and a plurality of optimal interventricular delays, storing the optimal atrio-ventricular delays and the optimal interventricular delays in association with corresponding patient activity states, detecting a change in patient activity, adjusting an atrial pacing rate in response to the detected change in patient activity based at least in part on a heart failure status and setting the atrio-ventricular delay and the interventricular delay, in response to the detected change in patient activity, using a stored optimal atrio-ventricular delay that corresponds to the patient activity and a stored optimal interventricular delay that corresponds to the patient activity. Other exemplary technologies are also disclosed.

In general, the various methods, devices, systems, etc., described herein, and equivalents thereof, are suitable for use in a variety of pacing therapies and/or other cardiac related therapies.

BRIEF DESCRIPTION OF THE DRAWINGS

Features and advantages of the described implementations can be more readily understood by reference to the following description taken in conjunction with the accompanying drawings.

FIG. 4 is a diagram of various exemplary schemes that pertain to optimization of CRT response to changes in patient activity.

FIG. 5 is a series of plots that correspond to adjustments to patient activity for a normal patient and for a heart failure patient.

FIG. 15 is a series of equations for use in various exemplary methods for single ventricular pacing and/or bi-ventricular pacing therapies.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are used at times to reference like parts or elements throughout the description.

Overview

Exemplary techniques pertain generally to optimizing delivery of cardiac resynchronization therapy (CRT) as a function of patient activity. In particular, such techniques may be implemented in a post-operative phase to attenuate unfavorable remodeling of the heart and to promote patient activity during this phase. For example, various exemplary methods include adjusting atrial pacing rate in response to an increase in patient activity in a manner that helps to ensure a favorable patient opinion to the increased activity. Some examples pertain to adjusting atrial pacing rate during a recovery time as well. Further, various exemplary methods may acquire one or more CRT parameter values during a given patient activity state and then use or analyze these values to improve delivery of CRT at a future time. For example, to improve a patient's response to exercise, an exemplary CRT device may adjust atrial pacing rate and one or more CRT parameter values (e.g., AV and VV) based on historical information, which may have been acquired by the CRT device. As such, an exemplary CRT device may learn and use such learning to improve CRT delivery.

The following description begins with a discussion of exemplary implantable devices and associated components followed by a discussion of patient behavior toward activity. Next, various exemplary schemes are introduced followed by a discussion of various exemplary methods, devices, systems, etc.

Exemplary Stimulation Device

The techniques described below are intended to be implemented in connection with any stimulation device that is configured or configurable to stimulate nerves and/or stimulate and/or shock a patient's heart.

Figure 1:
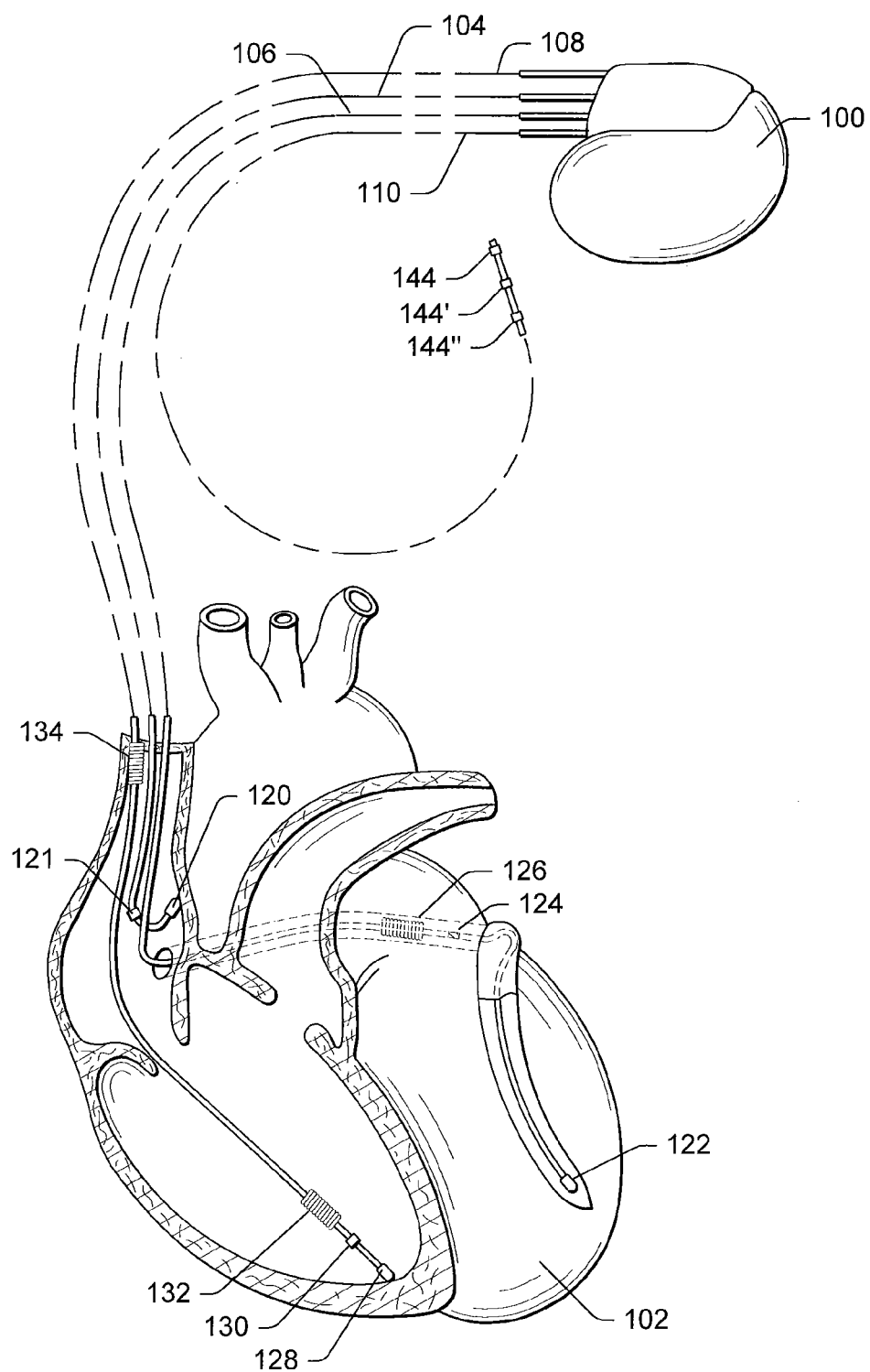
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of cardiac or other tissue (e.g., autonomic nerves, other nerves, muscle). Such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. The lead 104 may have other electrodes as well.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

The coronary sinus lead 106 optionally includes electrodes for stimulation of autonomic nerves. For example, an exemplary coronary sinus lead includes pacing electrodes capable of delivering pacing pulses to a patient's left ventricle and at least one electrode capable of stimulating an autonomic nerve (e.g., for control of autonomic tone, etc.).

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
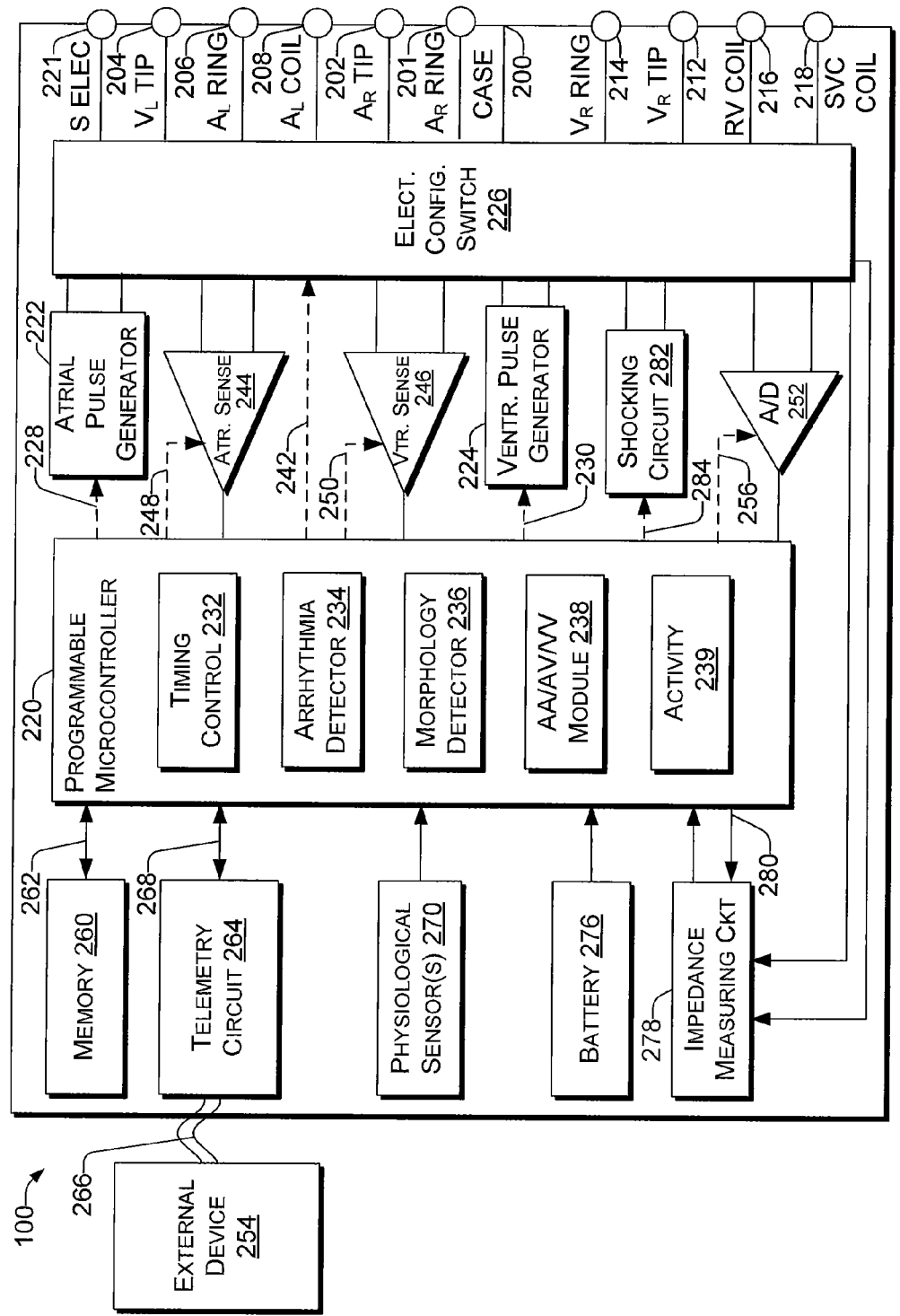
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable electrodes is also possible via a stimulation terminal S ELEC 221.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable electrodes is also possible via the stimulation terminal S ELEC 221.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (e.g., PV/AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, bi-ventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays.

The microcontroller 220 of FIG. 2 also includes an activity module 239. This module may include control logic for one or more activity related features. For example, the module 239 may include an algorithm for determining patient activity level, calling for an activity test, calling for a change in one or more pacing parameters, etc. These algorithms are described in more detail with respect to the figures. The module 239 may be implemented in hardware as part of the microcontroller 220, or as software/firmware instructions programmed into the device and executed on the microcontroller 220 during certain modes of operation. The module 239 may act cooperatively with the AA/AV/VV module 238.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation) are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGMs) and status information relating to the operation of the device 100 (as contained in the microcontroller 220 or memory 260) to be sent to the external device 254 through an established communication link 266.

The stimulation device 100 can further include one or more physiologic sensors 270. For example, a physiologic sensor may be a "rate-responsive" sensor used to adjust pacing stimulation rate according to activity state of a patient. The one or more physiological sensors 270 may include a sensor to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that a physiologic sensor may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

The one or more physiological sensors 270 optionally include a minute ventilation sensor (e.g., where minute ventilation is defined as the total volume of air that moves in and out of a patient's lungs in a minute). Signals generated by a sensor can be passed to the microcontroller 220 for analysis in determining whether to adjust the pacing rate, etc. In various configurations, the microcontroller 220 monitors signals for indications of activity status. Where a device includes a position sensor (e.g., accelerometer), the device may determine, for example, whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Techniques to Improve Patient Response to Changes in Activity

Figure 3:
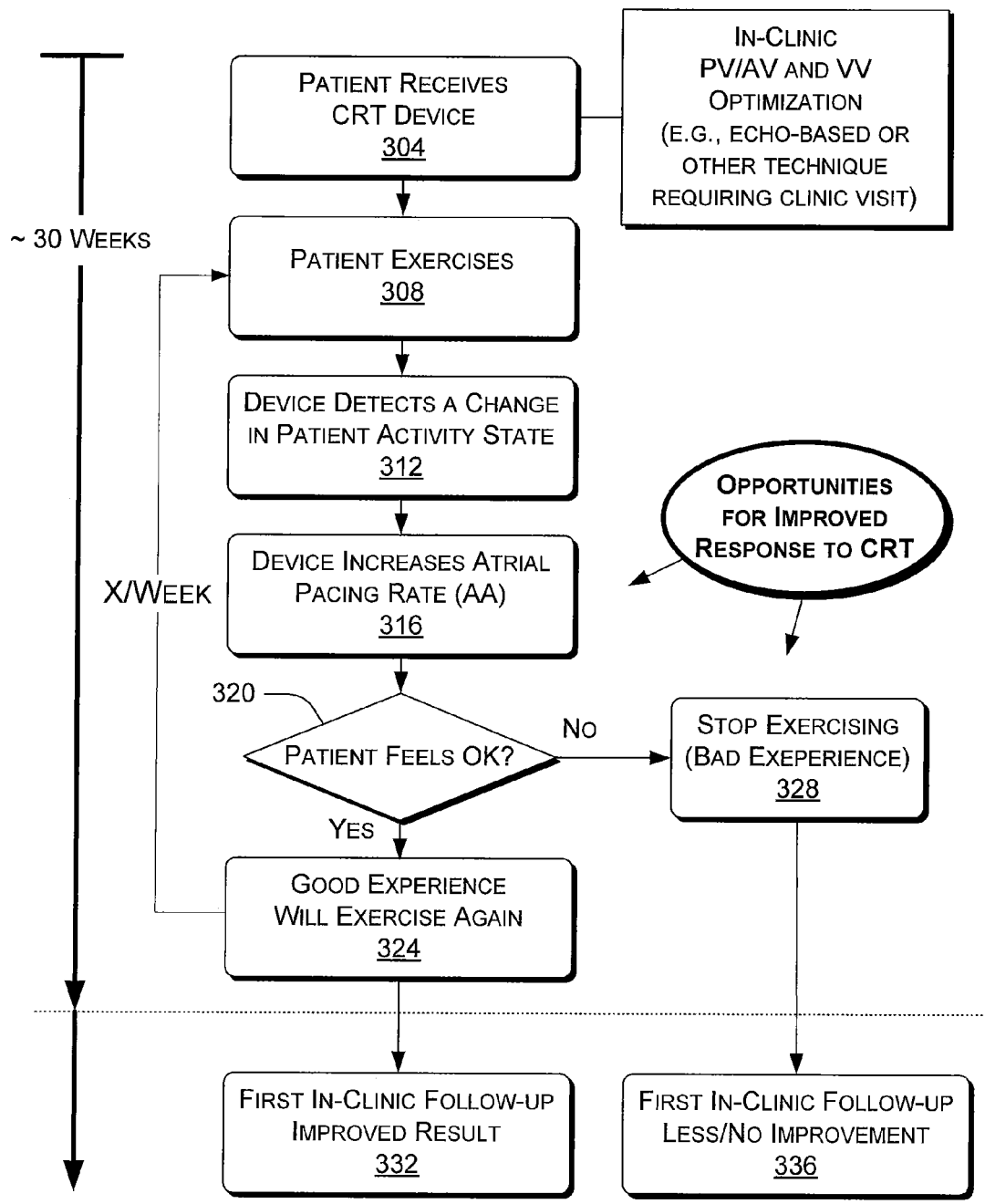
FIG. 3 is a diagram illustrating patient behavior in a time period following implantation of a CRT device and identifying opportunities to improve response to CRT.

FIG. 3 shows a flowchart of patient behavior post-CRT implant 300 that includes a phase between time of implant and a first in-clinic follow-up visit. This phase typically covers a time period from a couple of months (e.g., about 2 months) to about 6 months and is referred to as a post-operative phase or a preliminary recovery phase. Prior to implantation of a CRT device, a heart failure patient may be lethargic, experience bouts edema and, in general, have a somewhat unsatisfactory quality of life. Hence, a CRT device aims to improve quality of life, in particular, by increasing cardiac performance. In turn, with increased cardiac performance, a patient can become more active and feel better. Indeed, after implantation of a CRT device, studies indicate that patient activity has a significant benefit on quality of life (see, e.g., Giannuzzi, et al., "Attenuation of Unfavorable Remodeling by Exercise Training in Postinfarction Patients With Left Ventricular Dysfunction" *Circulation.* 1997; 96:1790-1797).

In the instance where a patient receives a CRT device shortly after suffering an infarct, patient activity (e.g., exercise) can play attenuate unfavorable post-infarct remodeling. End-diastolic volume, end-systolic volume, and regional dilatation can be maintained by exercise whereas without exercise they can increase significantly. Ejection fraction and wall motion abnormalities can also be improved significantly by exercise. With respect to general well-being, social anxiety, easy-goingness, symptoms perceived during daily physical activity, and general well-being can increase significantly by exercise.

Overall, the beneficial effect of cardiac rehabilitation exercise training on exercise tolerance and symptoms is one of the most clearly established favorable outcomes, even in patients with severely depressed ventricular function and compensated chronic heart failure, and particularly in those with decreased functional capacity. Hence, it is desirable to create a post-implant environment that promotes exercise.

As discussed with respect to the schematic 300 of FIG. 3, opportunities exist to create an environment that promotes exercise in patients receiving a CRT device. The schematic 300 commences in an implantation block 304 where a patient receives a CRT device. At this point in time, the CRT device operates according to one or more algorithm with parameters set according to an in-clinic examination of the patient. For example, a clinician may acquire an echocardiogram and use echocardiograph information to set a PV parameter, a AV parameter and a W parameter. Importantly, at this point in time, the patient is in a post-operative state and may not be feeling very well. Further, a patient typically recognizes few, if any, cardiac remodeling benefits and/or psychological benefits of CRT device implantation at this point in time. Hence, the parameters can be, at best, an estimate as to optimal parameters for the patient in the coming months. This fact is recognized by the need for a first in-clinic follow-up where another echocardiogram may be acquired and analyzed to determine more optimal parameters for the one or more algorithms of the CRT device.

To understand better behavior between the time of implant and the first in-clinic follow-up visit, the schematic 300 includes a patient exercise block 308 to indicate how a CRT device may respond to patient exercise. As a patient exercises, a CRT device may use one or more techniques to detect an increase in patient activity or cardiac demand, per a detection block 312, and, in response to this detection, increase heart rate by shortening an AA interval for atrial pacing, per an atrial pacing rate block 316.

Importantly, a decision block 320 represents how a patient feels at this point in time. For example, the decision block 320 may consider if the patient felt that the CRT device performed adequately. A CRT device may not respond quickly enough to increased patient activity, it may respond too quickly, it may respond with too high of an atrial rate, it may respond with an atrial rate that is perceived by the patient as being too high, it may respond with an atrial rate that is too low, it may respond with an atrial rate that is perceived as being too low, etc. Further, while not shown explicitly in the schematic 300 of FIG. 3, after exercise, a CRT device may not "cool down" adequately. Hence, a patient may "react" to a CRT device's performance when commencing exercise, during exercise and/or at the termination of exercise. Per the decision block 320, if a patient experiences or perceives CRT device performance in a negative light (i.e., a bad experience), the patient may stop exercising, per the stop exercising block 328. However, if the patient has a good experience, then the patient may be more likely to exercise again, per the exercise again block 324.

The good outcome of block 324 and the bad outcome of block 328 can be expected to have an effect on results of CRT noted during the first in-clinic follow-up visit. In particular, for the exercising patient, the in-clinic examination can be expected to demonstrate an improved result, per block 332; whereas, for the patient that does not exercise, the in-clinic examination can be expected to demonstrate less or no improvement (e.g., compared to the hypothetical situation where the patient had exercised).

As indicated in the schematic 300, opportunities exist for improved response to CRT. In particular, opportunities exist to take action in the post-operative recovery period prior to the first in-clinic follow-up visit. More specifically, opportunities exist to respond more appropriately to an increase in patient activity, to patient activity and to a decrease in patient activity. Further, as described herein, an exemplary CRT device optionally adjusts PV, AV and/or VV parameters during the post-operative recovery period. Such a CRT device may actually optimize one or more parameters during the post-operative recovery period, for example, in a manner based on a patient's activity state.

Various exemplary techniques are described herein to optimize algorithms for CRT. Some of these techniques use information from a QUICKOPT™ CRT parameter optimization algorithm (St. Jude Medical Corp, Sylmar, Calif.). Programming of appropriate PV and/or AV and VV delays (timing cycle parameter optimization) has shown to be effective at improving patient outcomes by increasing cardiac output and reducing non-responder rates. Various CRT optimization algorithms are disclosed in co-pending U.S. patent application Ser. No. 10/703,070, filed Nov. 5, 2003, entitled "Methods for Ventricular Pacing", which is incorporated herein by reference. An optimization algorithm may operate in a relatively short period of time, for example, typically less than about 90 seconds.

Clinical evidence demonstrates that timing cycle optimization improves outcomes to CRT. Various studies indicate that about 80% of patients showed statistically significant improvement in markers including quality of life score (QoP), NYHA class improvement, and reduction in non-responder rates, resulting from sequential biventricular pacing over simultaneous pacing. Clinical evidence also demonstrates that optimal delays change over time, so regular optimization is desirable.

In a conventional scenario, a CRT optimization algorithm executed by an external implantable CRT device programmer can optimize AV, PV, and VV intervals in about a minute (e.g., by pushing a single button). While this conventional scenario occurs in a clinic (i.e., requires a clinical visit), it can reduce or eliminate the need for echocardiography-based optimization. Such an algorithm allows for optimization of both non-responders and responders. Such an algorithm allows for frequent optimization in response to changing timing cycles. Such an algorithm is compatible with many multi-chamber ICDs (e.g., DR and HF). Again, in general, echocardiography-based optimization is time consuming as it requires an in-clinic visit and a skilled clinician. Further, echocardiograph can be impractical for optimizing all patients. Yet further, echocardiography is best performed with a stationary patient in a rest state. Thus, echocardiography is not ideal for acquiring cardiac information when a patient is active.

Various exemplary techniques can account for different patient activity levels or states, for example, as indicated by one or more activity sensors (e.g., MV, accelerometers, etc.). An exemplary technique can use a difference between CRT parameter information for a mild active state and CRT parameter information for a rest state as an indicator of specific electrophysiological conditions of HF patients, which typically consist of multiple factors. For example, a significant population of HF patients have left bundle branch block (LBBB) that causes slow LV conduction, chronotropic incompetence, a need for beta blocker therapy, etc. With LBBB, a higher atrial pacing rate (e.g., triggered in response to an increase in patient activity) may result in mild or first degree heart block. Thus, a need exists to tailor CRT algorithms for a HF patient with LBBB or other conduction problems.

An exemplary technique tailors CRT response to HF patient needs (i) at initiation of exercise, (ii) during exercise and/or (iii) termination of exercise. Such a technique can detect a change in intrinsic heart rate from a rest state to one or more other activity states, and vice versa, and store noted changes and/or activity states in combination with results from a QUICKOPT parameter optimization algorithm (e.g., at rest and one or more other activity states). Results from a QUICKOPT optimization test, whether at rest or at another activity state, can include duration of atrial signals (e.g., atrial wave width), atrio-ventricular conduction delays to RV and LV leads (e.g., $PR_{RV}$, $PR_{LV}M$, interventricular conduction delays and difference of left-to-right interventricular conduction delay (IVCD-LR) and right-to-left interventricular conduction delay (IVCD-LR).

An exemplary technique can use changes in test results to tailor rate adaptive algorithms. For example, if intrinsic rate is elevated above some intrinsic rate threshold, a rate adaptive algorithm can commence atrial pacing in a controlled manner to reach a target atrial rate that corresponds with a particular patient activity state. In this example, the target atrial rate may be predetermined to meet the patient needs. In some instances, an exemplary technique may operate according to stored information in a manner where, in a conventional sense, a rate adaptive algorithm is not needed or enabled.

In instances where a patient's intrinsic heart rate is lower than a predetermined intrinsic rate threshold, results from a CRT parameter optimization algorithm can be analyzed. For example, an exemplary technique can periodically acquire results from a CRT parameter optimization algorithm and automatically analyze the results for purposes of more optimally responding to changes in patient activity. For example, if a measured PR delay or PV parameter value is prolonged compared at an active state, compared to a control state (e.g., a rest state), an exemplary adaptive pacing scheme can respond accordingly by adjusting one or more CRT parameters. Alternatively, such a scheme may determine that such a response is not appropriate for a given patient. Similarly if a measured PR delay is short or has shortened compared to a predetermined value or previous measured value, an exemplary adaptive pacing scheme may respond accordingly. While these examples mention PR and PV, other results generated by a CRT parameter optimization algorithm can also be utilized (e.g., IVCD, PV and AV delays, the duration of atrial signals, etc.). An exemplary adaptive pacing scheme may use one or more of such CRT parameter optimization results.

In various examples, an exemplary adaptive pacing scheme includes features of one or more existing adaptive pacing schemes. For example, a conventional adaptive pacing scheme includes use of a "rest rate" and a "base rate". More specifically, a rest rate for a particular patient may be set to approximately 50 bpm and a base rate set to approximately 70 bpm. An exemplary adaptive pacing scheme, when one or more conditions are met, can be enabled to raise or lower atrial rates according to a predetermined pattern for more optimally accelerating atrial rate for a patient commencing exercise and for more optimally decelerating atrial rate for a patient terminating exercise and returning to rest. Again, information acquired using a CRT parameter optimization algorithm can be used to tailor rate adaptive schemes and thereby provide for more optimal responses to patient activity state changes and more optimal CRT delivery while a patient is in any particular patient activity state.

FIG. 4 shows five exemplary schemes 410, 420, 430, 440 and 450. Scheme 410 pertains to an optimization algorithm for PV/AV and VV that is implemented by an implantable device at least during the first 6 months post-CRT implantation. As already mentioned, such a scheme can improve patient response to CRT and overall outcome. Such a scheme can reduce or alleviate the need for in-clinic visits to perform echocardiographic or other optimization that relies on external equipment.

Scheme 420 pertains to an optimization algorithm for PV/AV and VV that is implemented by an implantable device where the acquired or determined PV/AV and VV occur in conjunction with patient activity information. Such a scheme can acquire or determine PV/AV and VV information and associate this information with one or more activity states or activity state transitions. In turn, such activity-associated information can be used to optimize a CRT device's response to an activity state and/or a transition between activity states.

Scheme 430 pertains to an optimization algorithm for PV/AV and VV that is implemented by an implantable device in a manner responsive to patient activity. Such a scheme can improve response to commencement of exercise, to exercise and to termination of exercise. In essence, such an algorithm knows how to respond to such activity states and/or transitions between activity states or is otherwise instructed as to how to respond (e.g., by a rate adaptive pacing algorithm).

Scheme 440 pertains to an optimization algorithm for heart rate (e.g., a rate adaptive pacing algorithm) that is implemented by an implantable device and that can respond to patient activity and a patient's physical condition (e.g., heart failure status). Such a scheme can improve rate response to exercise, for example, to attenuate unfavorable remodeling and to improve quality of life.

Scheme 450 pertains to an optimization algorithm for heart rate and PV/AV and W that is implemented by an implantable device and that can respond to patient activity and a patient's physical condition (e.g., heart failure status). Such a scheme can improve CRT response to exercise, for example, to attenuate unfavorable remodeling and to improve quality of life.

Schemes 420, 430, 440 and 450 include responding to patient activity while scheme 410 includes optimizing PV/AV and VV by an implantable device, at least during the first six months post-CRT implantation.

With respect to algorithms that respond to patient activity, often referred to as rate adaptive pacing algorithms, FIG. 5 shows how a rate adaptive pacing algorithm may select a pacing rate in response to patient activity for a normal patient 510 and for a heart failure patient 520. FIG. 5 also shows some rate adjustment parameters 530 and how values for these parameters compare for a normal patient and a heart failure patient. The parameters include an increased activity threshold ($Th_{IA}$) for triggering a change in pacing rate in response to an increase in activity state, a decreased activity threshold ($Th_{DA}$) for triggering a change in pacing rate in response to a decrease in activity state, a rate responsive slope ($Slope_{R/A}$) for determining how to select a maximum sensor rate based on a patient's activity and a maximum deliverable rate, which is the maximum rate that a CRT device can deliver according to a rate adaptive pacing algorithm.

Referring to the plot 510, a relationship exists for selecting a pacing rate based on patient activity for a "normal" patient (e.g., a patient fitted with a cardiac pacing device yet, for example, not categorized by a high NYHA class such as class III or IV). The plot 510 may be used to select a pacing rate upon detection of an increase in patient activity state. For example, as patient activity exceeds $Th_{IA}$, the algorithm will determine an appropriate maximum sensor rate based on the portion of the relationship having $Slope_{R/A}$. How an algorithm calls for the maximum sensor rate (i.e., target rate) to be implemented or reached is discussed with respect to FIG. 6 (e.g., immediate call for target rate or adjustment to target rate over a response time period). Also, relationships may differ between an increase in activity and a decrease in activity. In other words, some path hysteresis may exist depending on whether a patient has an increase in activity or a decrease in activity.

Referring to the plot 520, a relationship exists for selecting a pacing rate based on patient activity for a heart failure patient (e.g., a patient diagnosed with heart failure and optionally classified in NYHA class III or IV). In this example, the threshold values for $Th_{IA}$ and $Th_{DA}$ are less than those for the normal patient. In particular, a heart failure patient may not be capable of any significant elevation in intrinsic rate and thus atrial pacing becomes more important at a lower level of patient activity. Further, $Slope_{R/A}$ may be steeper as a small change in patient activity can benefit from an increase in pacing rate. However, the maximum deliverable pacing rate may be less than that of a normal patient as a heart failure patient may not benefit from pacing rates that could benefit a normal patient. Thus, as described herein, a heart failure patient can benefit from a customized or learned relationship between patient activity and pacing rate. Further, such a customized or learned relationship may account for an increase in patient activity and/or a decrease in patient activity. In other words, an exemplary adaptive pacing rate algorithm may adjust pacing rate differently depending on whether a patient's activity is increasing or decreasing. Such an adaptive pacing rate algorithm corresponds to the exemplary scheme 440 of FIG. 4.

Figure 6:
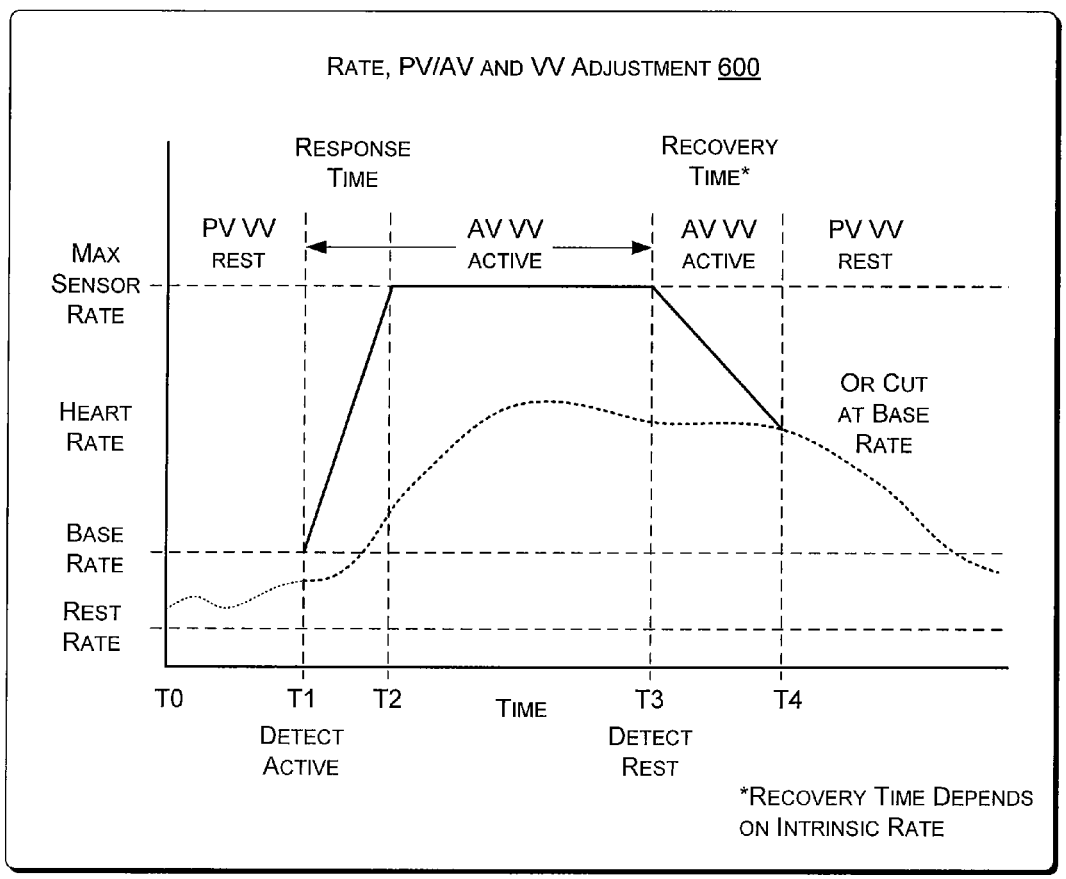
FIG. 6 is a plot of heart rate versus time over a time period that includes an increase in patient activity and a decrease in patient activity.

As the plots 510 and 520 of FIG. 5 do not explicitly account for time, FIG. 6 shows a plot 600 of a scenario that includes a response time and a recovery time surrounding a period of exercise (i.e., elevated patient activity). The plot 600 shows heart rate, whether intrinsic or paced, versus time. Some parameter based heart rates are also shown and include rest rate, base rate and maximum sensor rate. The rest rate may be set to a rate, for example, of about 45 pulses per minute to provide a bottom below which the heart rate will not fall. For example, a patient can have a physiologic slowing of his or her heart rate during a period of profound rest. The base rate may be set to an appropriate rate for a heart failure patient to operate as a starting point when a need for even higher rates exists. The maximum sensor rate, as explained with respect to FIG. 5, is the target rate to be achieved according to a relationship between patient activity and desired or beneficial heart rate. The plot 600 of FIG. 6 also introduces CRT parameter settings and adjustments that may occur with respect to one or more changes in patient activity.

Figure 7:
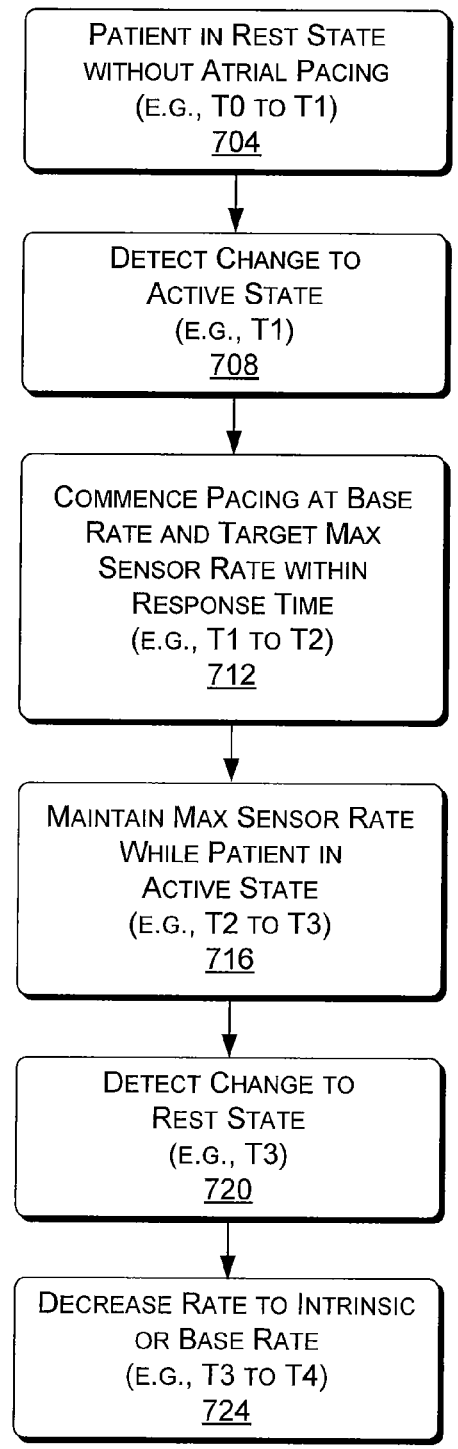
FIG. 7 is a block diagram of various events or actions that occur during the time period covered by the plot of FIG. 6.

FIG. 7 shows a block diagram 700 of various observations or actions that can occur with respect to time for the plot 600 of FIG. 6. Per block 704, at times T0 to T1, a patient is in a rest state where the patient's intrinsic rate may fluctuate within a band between the rest rate and the base rate for a given activity state. Further, CRT parameters for PV and VV may be selected based on this activity state and the fact that the patient's intrinsic rate is between the rest rate and the base rate.

Per block 708, at time T1, detection of a change in patient activity occurs. According to an adaptive pacing rate algorithm, a call is made to increase the patient's rate to the base rate and to increase the rate further to a target rate (i.e., a maximum sensor rate that corresponds to the detected activity state). In the example of FIG. 7, the detection and call for an increase in rate commence a response time. Per block 712, the response time spans time period T1 to T2. This response time may be determined according to any of a variety of techniques. For example, as described herein, an exemplary technique determines a response time for a patient based on information acquired during prior changes in patient activity. Using such information, such a technique may tailor the response time such that a patient has a "good" experience (see, e.g., the block 324 of FIG. 3). Again, a bad experience (see, e.g., the block 328 of FIG. 3) may cause a patient to refrain from exercise or to exercise less often.

As discussed herein, an exemplary technique may, in addition to calling for a rate and a response path or time, call for an adjustment to one or more CRT parameters. More specifically, in the example of FIG. 6, as atrial pacing is used to achieve adequate cardiac performance, an adjustment needs to occur from use of PV to AV. Further, such a change may require an adjustment to VV as well. According to an exemplary technique, rate response and CRT parameter adjustment occur in a coordinated manner. For example, upon a call for an increase in heart rate, an exemplary algorithm may select AV and/or VV parameter values that correspond to the target rate (i.e., maximum sensor rate) or that correspond to the underlying detected patient activity state.

Referring again to the plot 600, at time T2, the maximum sensor rate is achieved. This action is also indicated in block 716 of FIG. 7 as maintaining the maximum sensor rate while the patient is in the active state (e.g., for the time period from T2 to T3). At some point in time, indicated by time T3, the patient may stop exercising or otherwise decrease activity. As indicated by block 720 of FIG. 7, such a decrease in activity is detected at time T3 and, per block 724, one or more actions follow with respect to recovery time, atrial pacing rate, PV/AV, VV, etc.

The plot 600 shows a decreasing atrial pacing rate from time T3 to time T4, at which point the atrial pacing rate and the underlying intrinsic rate meet. Such a condition may be noted, for example, by an intrinsic atrial beat appearing in an electrocardiogram. At this point in time, an exemplary technique can terminate atrial pacing (noting that the intrinsic rate is above the base rate) and can also set PV and adjust VV, as desired.

Overall, the plot 600 and the flowchart 700 demonstrate how rate adjustments may occur with respect to time to benefit heart failure patients and how such rate adjustments may be coordinated with changes to one or more CRT parameters.

While the plot 600 and flowchart 700 show affirmative actions, data acquisition and data storage may accompany such actions. For example, between times T0 and T1, an exemplary optimization algorithm may optimize PV and/or VV and store such information in association with an average intrinsic rate or patient activity state during the time period T0 to T1. Similarly, such an algorithm may optimize AV and/or VV and store such information in association with an atrial pacing rate or patient activity state during the time period T2 to T3. In addition, an exemplary algorithm may acquire information during a response time and/or during a recovery time. Yet further, where a response time or a recovery time is of sufficient duration, an algorithm may optimize AV and/or VV. Given such optimized parameter values, in association with rate or activity information, an exemplary algorithm may use these values in the future. As described herein, such optimized parameter values may be analyzed to generate value for future use. For example, a model may be developed using the optimized parameter values and associated rates and/or activity states and the model used for enhanced delivery of CRT.

Figure 8:
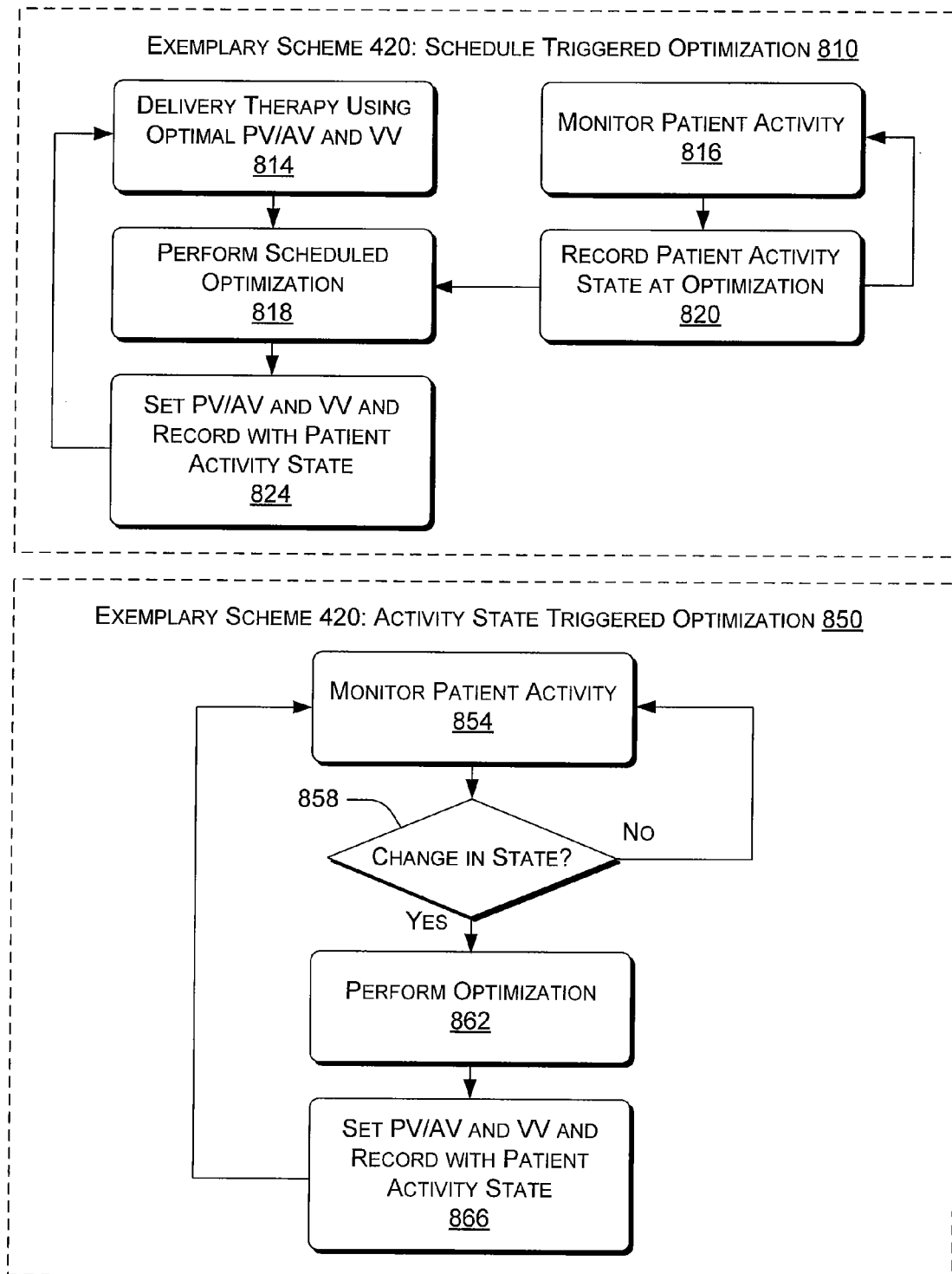
FIG. 8 is a block diagram of an exemplary method for optimizing one or more CRT parameter values according to a schedule and of an exemplary method for optimizing one or more CRT parameter values in response to a change in patient activity.

FIG. 8 shows two exemplary variations of the scheme 420 of FIG. 4: a schedule triggered optimization variation 810 and an activity state or rate triggered optimization variation 850. In the variation 810, a delivery block 814 delivers CRT using optimal PV/AV and VV while a monitoring block 816 monitors patient activity. A performance block 818 calls for performing a scheduled optimization of PV/AV and VV. At this point, a recordation block 820 records a patient's activity state in correspondence with the optimization. A set block 824 follows the optimization or is the result of the optimization where optimized PV/AV and VV parameter values are used for CRT delivery and where these optimized parameter values are stored or otherwise noted in conjunction with the patient's activity state per the recordation block 820.

The variation 850 includes a monitor block 854 to monitor patient activity. A decision block 858 uses information (e.g., sensed by an activity sensor, etc.) to decide if a change occurred in patient activity state. If no change occurred, then the scheme returns to the monitor block 854, noting that such monitoring may occur in a relatively continuous manner throughout the scheme. In the instance the decision block 858 decides a change occurred (e.g., an increase or a decrease in patient activity), then the scheme enters a performance block 862 that calls for optimization of one or more CRT parameter values. A set block 866 follows the optimization or is the result of the optimization where optimized PV/AV and VV parameter values are used for CRT delivery and where these optimized parameter values are stored or otherwise noted in conjunction with the patient's activity state per the decision block 858.

Figure 9:
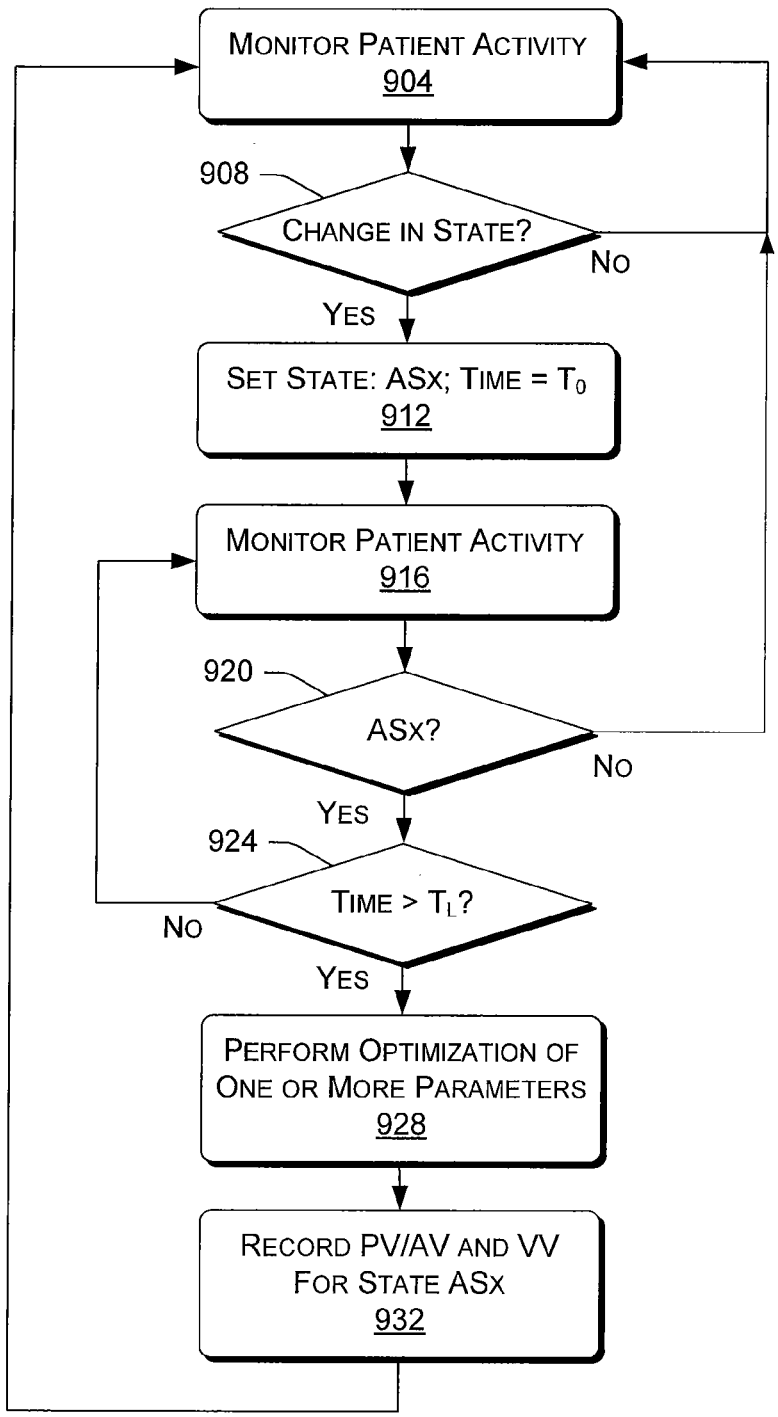
FIG. 9 is a block diagram of an exemplary method optimizing one or more CRT parameter values if a patient has been in a particular activity state for a predetermined period of time.

FIG. 9 shows a more detailed exemplary method for patient activity triggered optimization of one or more parameters 900. The method 900 commences in a monitor block 904 for monitoring patient activity. For example, as discussed with respect to the implantable device of FIGS. 1 and 2, an accelerometer, minute ventilation, or other techniques can be used to monitor patient activity and determine a patient activity state based on the activity. A decision block 908 decides if a change in patient activity state has occurred based on the monitoring. If the decision block 908 decides that a change has not occurred, then the method 900 may continue monitoring. Again, monitoring of patient activity may occur on a relatively continuous basis, for example, as a task performed by a processor according to some task priority, etc.

In the instance the decision block 908 decides that a change in state occurred, then the method 900 enters a set block 912 that sets a state indicator to an appropriate patient activity state (e.g., ASx) and that also notes a time for the change in state (e.g., Time=T0). As indicated by monitor block 916, monitoring of patient activity continues followed by another decision block 920 to decide if the patient is still in the noted activity state (e.g., ASx). If the decision block 920 decides that the patient has changed state, then the method 900 exits the time loop and continues to monitor patient activity, for example, per block 904. However, if the decision block 920 decides that the patient is still in the noted activity state (e.g., ASx), then the method 900 proceeds to yet another decision block 924 that decides if a certain amount of time has passed to indicate that the patient has been in the noted activity state for some predetermined period of time, indicated by time limit $T_L$.

If the decision block 924 decides that the time has not exceeded $T_L$, then the method 900 continues monitoring patient activity per block 916, which is still within the time loop defined by blocks 916, 920 and 924. However, if the decision block 924 decides that the time has exceeded the time limit $T_L$, then the method 900 performs optimization of one or more parameters. A recordation block 932 follows that records values for the one or more parameters in conjunction with the associated activity state (e.g., ASx).

In such a manner, an implantable device provides some insurance that a parameter optimization has occurred at a particular patient activity state. In turn, the optimized parameters for the particular state may be used for any of a variety of purposes. For example, CRT parameters may be set using values for optimized parameters upon detection of the patient activity state or upon a call for an atrial pacing rate associated with the patient activity state.

Figure 10:
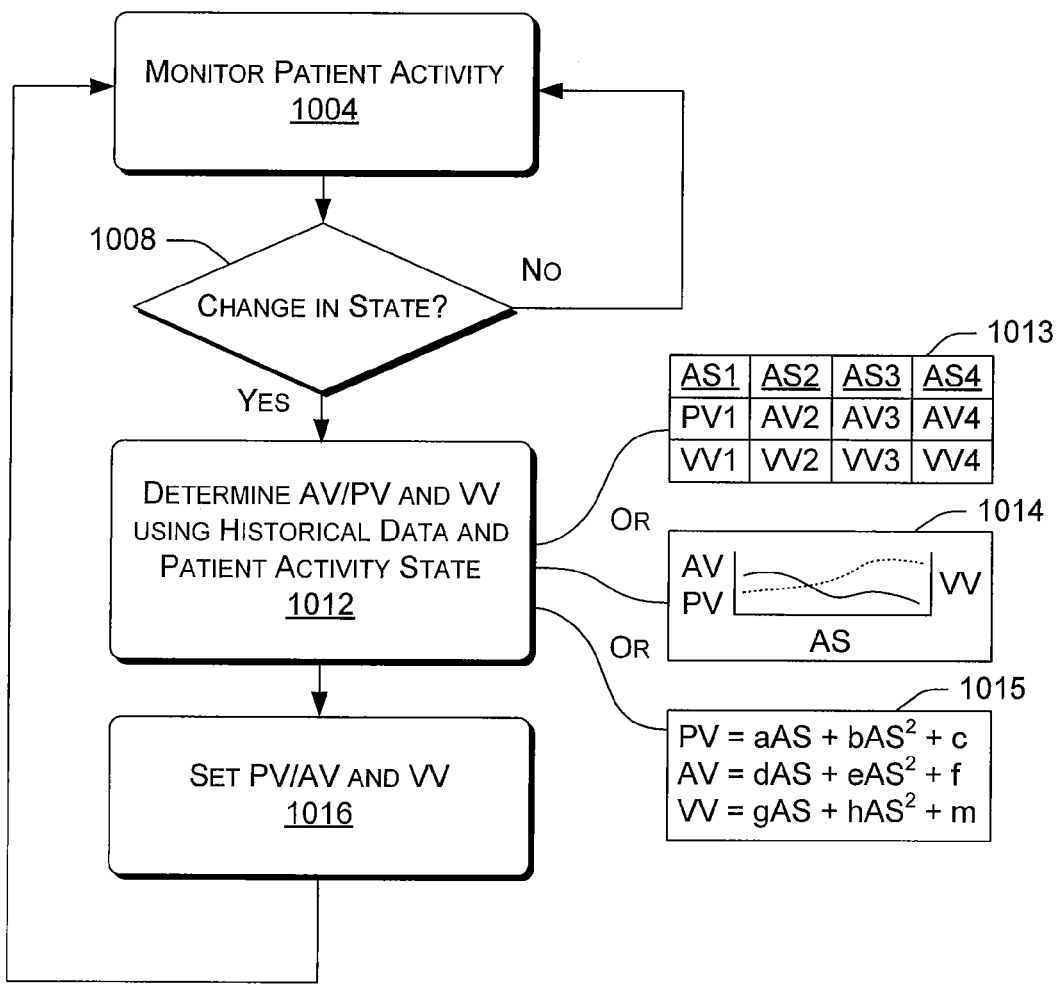
FIG. 10 is a block diagram of an exemplary method for setting one or more CRT parameter values in response to a change in patient activity state.

FIG. 10 shows an exemplary method 1000 that corresponds to the scheme 430 of FIG. 4. The method 1000 can adjust one or more CRT parameters upon a change in patient activity state. The method 1000 commences in a monitoring block 1004 for monitoring patient activity. A decision block 1008 decides if a change in activity state has occurred. If a change has not occurred, then the method 1000 continues to monitor patient activity while maintaining CRT parameter values. However, if a change has occurred, then the method 1000 responds in a determination block 1012 that determines an AV/PV and VV for the noted activity state based on historical data. For example, the determination block 1012 may use a table 1013 that associates activity states and CRT parameter values. The table 1013 indicates that an activity state may be associated with an intrinsic heart rate (e.g., PV) while other activity states may be associated with an atrial paced rate (e.g., AV). The determination block 1012 may use trend information that can be represented in graphical form 1014 where a PV/AV and W are shown versus activity state. In another example, the determination block 1012 may use one or more models that model a CRT parameter as a function of activity state, as indicated by equations 1015 (e.g., an equation for PV, an equation for AV and an equation for VV). Once the determination block 1012 determines the one or more parameter values, then a set block 1016 sets one or more CRT parameters accordingly. The method 1000 may then continue monitoring patient activity per the monitor block 1004. As already mentioned, monitoring may continue on a relatively regular basis throughout any particular method, where desired or suitable.

Figure 11:
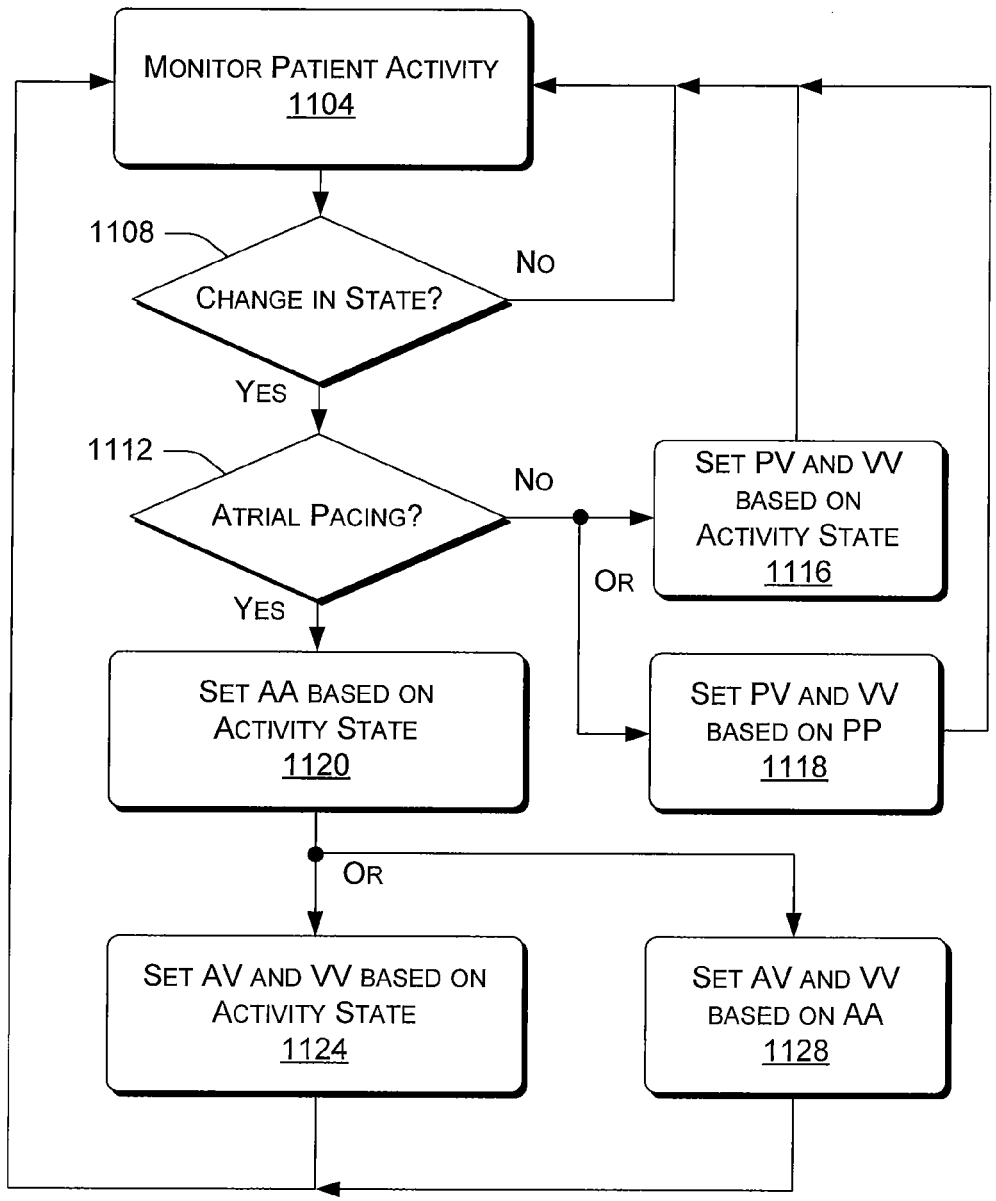
FIG. 11 is a block diagram of an exemplary method for setting one or more CRT parameter values based on a patient activity state or based on an intrinsic or an atrial pacing rate.

FIG. 11 shows an exemplary method 1100 associated with the exemplary scheme 430 of FIG. 4. In particular, FIG. 11 illustrates how one or more CRT parameters may be set according to patient activity or intrinsic rate or paced atrial rate. The method 1100 commences in a monitor block 1104 for monitoring patient activity. A decision block 1108 follows that decides if a change in patient activity state has occurred based on monitored information (e.g., MV, accelerometer, etc.). If no change has occurred, the method 1100 continues to monitor patient activity, for example, per the monitor block 1104. However, if a change has occurred in patient activity state, then the method 1100 enters another decision block 1112 that decides if atrial pacing is being used. If the decision block 1112 decides that atrial pacing is not being used, and hence intrinsic rate is controlling, then the method 1100 enters either a set block 1116 that sets PV and VV based on patient activity or a set block 1118 that sets PV and VV based on the intrinsic rate (PP).

If the decision block 1112 decides that atrial pacing is being used, then the method 1100 sets the atrial pacing rate (AA) to an appropriate value for the noted patient activity state. Given this atrial pacing rate (AA), the method 1100 may set AV and VV based on the atrial pacing rate as indicated by a set block 1128. Alternatively, a set block 1124 may be used to set AV and W based on the noted activity state.

Figure 12:
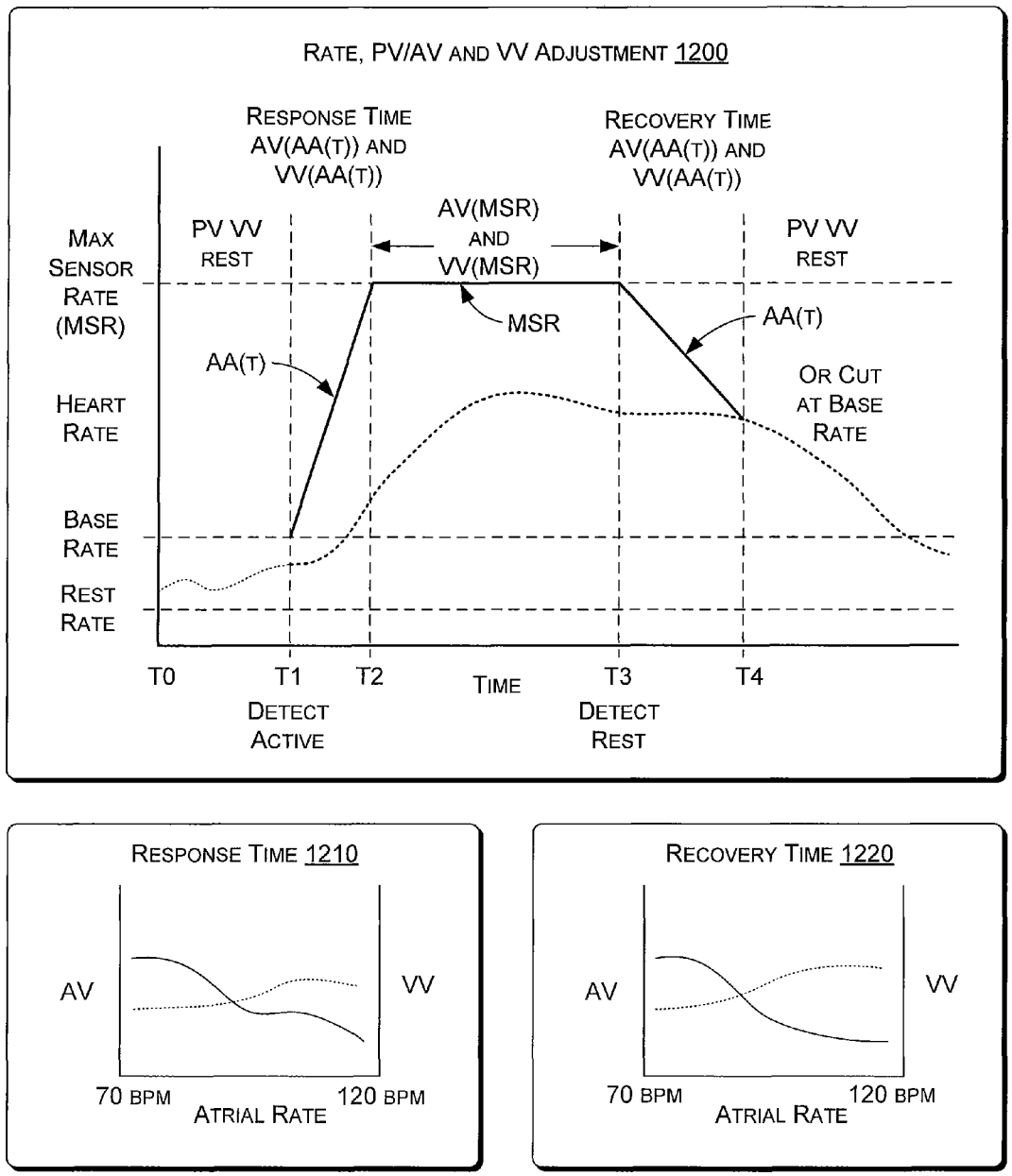
FIG. 12 is a plot of heart rate versus time, a plot of PV/AV and VV versus heart rate for a response time and a plot of PV/AV and VV versus heart rate for a recovery time where adjustments occur to one or more CRT parameter values during a response time and/or during a recovery time.

FIG. 12 shows a plot 1200 that includes various features of the plot 600 of FIG. 6, however, the plot 1200 includes additional features that can adjust one or more CRT parameter values during a response time and/or during a recovery time. Again, as mentioned with respect to FIGS. 3 and 4, a patient may form an opinion as to how a CRT device performs with respect to an increase and/or a decrease in patient activity. A positive opinion can promote patient activity while a negative opinion can diminish a patient's desire to be active. The adjustment techniques shown in FIG. 12 may be considered as within the exemplary scheme 450 of FIG. 4.

In the plot 1200, during the response time between times T1 and T2, AV and VV may be adjusted according to AA, which is a function of time. A plot 1210 includes PV/AV and VV plotted versus AA, such relationships may be used to determine one or more appropriate CRT parameter values.

While the plot 1200 shows a linear, continuous adjustment in atrial pacing rate, actual adjustment will typically occur in discrete steps. For example, during the time period between times T1 and T2, the atrial pacing rate may be adjusted using two or more steps. In a particular example, the response time is about 15 seconds and the atrial pacing rate is adjusted in three steps from T1 to T1+5 seconds, from T1+5 second to T1+10 seconds and a final step from T1+10 seconds to T1+15 seconds where the atrial pacing rate is set to the maximum sensor rate (MSR). In turn, each step may have an associated set of CRT parameter values. In combination, such a method aims to respond to an increase in patient activity in an optimal manner.

In general, a CRT device should respond to an increase in patient activity in a manner that suits the patient. An exemplary method may determine appropriate response times based on an underlying increase in intrinsic rate, based on a slope of increase in patient activity as measured by an activity sensor, based on a minute ventilation information, etc. If a response time is too short, a risk exists that a patient may be surprised by a sudden change in atrial pacing rate and/or adjustment to one or more CRT parameter values. On the other hand, if a response time is too long, a patient may experience some difficulty in achieving a desired activity state as the CRT device lags behind the patient's activity. Thus, a patient can benefit from a CRT device that responds in a manner that is acceptable for the patient.

The plot 1200 also includes a recovery time from time T3 to time T4. In general, the recovery time is longer than the response time. For example, a recovery time may be a minute or more. In the example of FIG. 12, a so-called hand-off algorithm halts atrial pacing once the underlying intrinsic rate meets the atrial pacing rate during recovery. For some patients, such a condition may not occur, for example, such a condition may not occur for pacing dependent patients that rely on atrial pacing during and after exercise.

In the plot 1200, during the recovery time between times T3 and T4, AV and VV may be adjusted according to AA, which is a function of time. A plot 1220 includes PV/AV and VV plotted versus AA, such relationships may be used to determine one or more appropriate CRT parameter values. The relationships in the plot 1210 and the plot 1220 may differ to account for underlying differences between response to activity and recovery from activity. By decoupling, at least to some extent, parameter values for response to exercise and parameter values for recovery from exercise, an exemplary CRT device may promote exercise and, in turn, help attenuate unfavorable cardiac remodeling.

An exemplary method accounts for a patient being assessed as having ischemic heart disease (IHD), coronary artery disease (CAD) or some combination of both (IHD/CAD). While a number of disease processes other than atherosclerosis can involve coronary arteries, in general, the term CAD refers to the atherosclerotic narrowing of the major epicardial coronary arteries. IHD is defined as a form of heart disease, with its primary manifestations resulting from myocardial ischemic, most commonly caused by atherosclerotic CAD, however, the term IHD encompasses a spectrum of disease ranging from the asymptomatic pre-clinical phase to acute myocardial infarction (AMI) and sudden death. Myocardial ischemia may occur in the absence of obstructive CAD, as in the case of aortic valve disease, hypertrophic cardiomyopathy, idiopathic dilated cardiomyopathy, and luetic aortitis.

Such a method may account for patient age, noting that younger patients tend to be more active than older patients. Further, geographic differences may exist (e.g., data suggest that Europe tends to have more younger patients treated for IHD compared to the United States, which treats more older patient for CAD). As explained with respect to FIG. 3, a CRT patient that has a favorable response to exercise is likely to exercise and experience an improvement in cardiac condition. A clinician can program a CRT device based in part on patient disease (e.g., IHD, CAD, IHD/CAD) such that the device adjusts response time and/or recovery time in a manner that increases patient likelihood of a favorable response to exercise.

An exemplary method accounts for patient heart failure status. For example, adjustments to rate, PV/AV and/or VV may occur based at least in part on NYHA class. Such a method may consider evidence of and/or location of heart damage, QRS characteristics (e.g., QRS width), drug treatment (e.g., beta blockade), etc.

Figure 13:
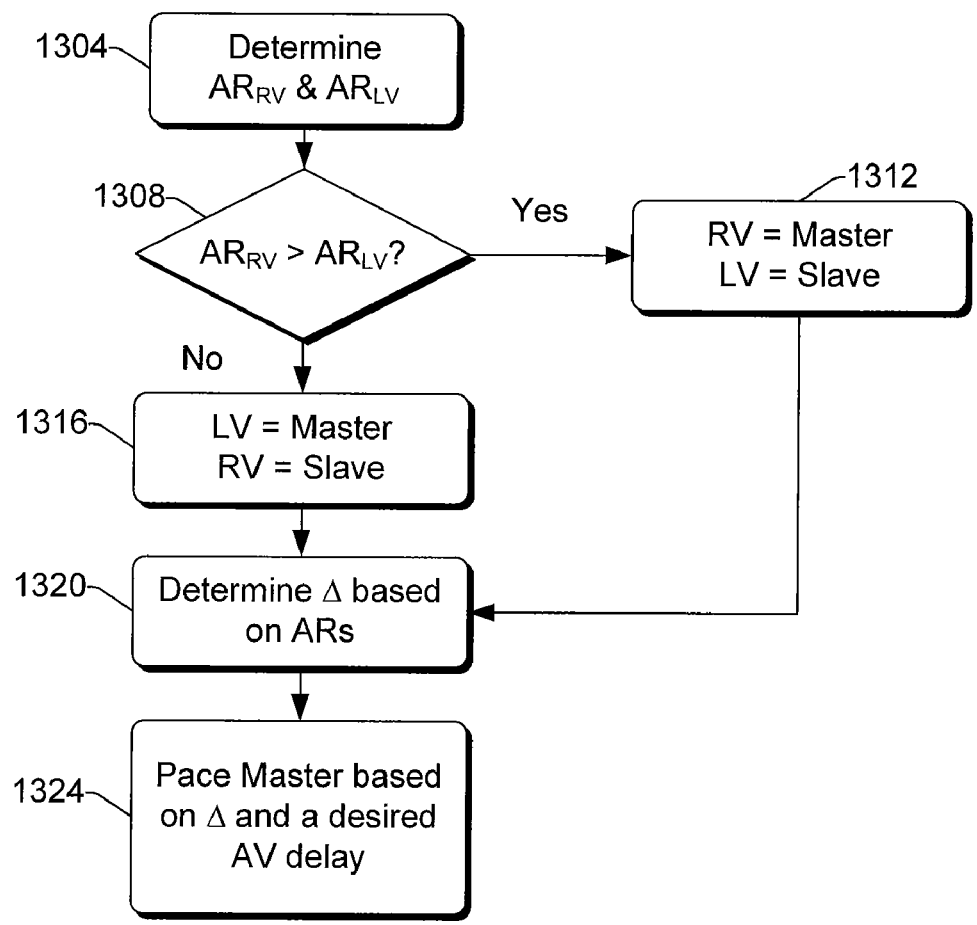
FIG. 13 is a block diagram of an exemplary method for ventricular pacing based on an $AR_{RV}$ time and an $AR_{LV}$ time.
Figure 14:
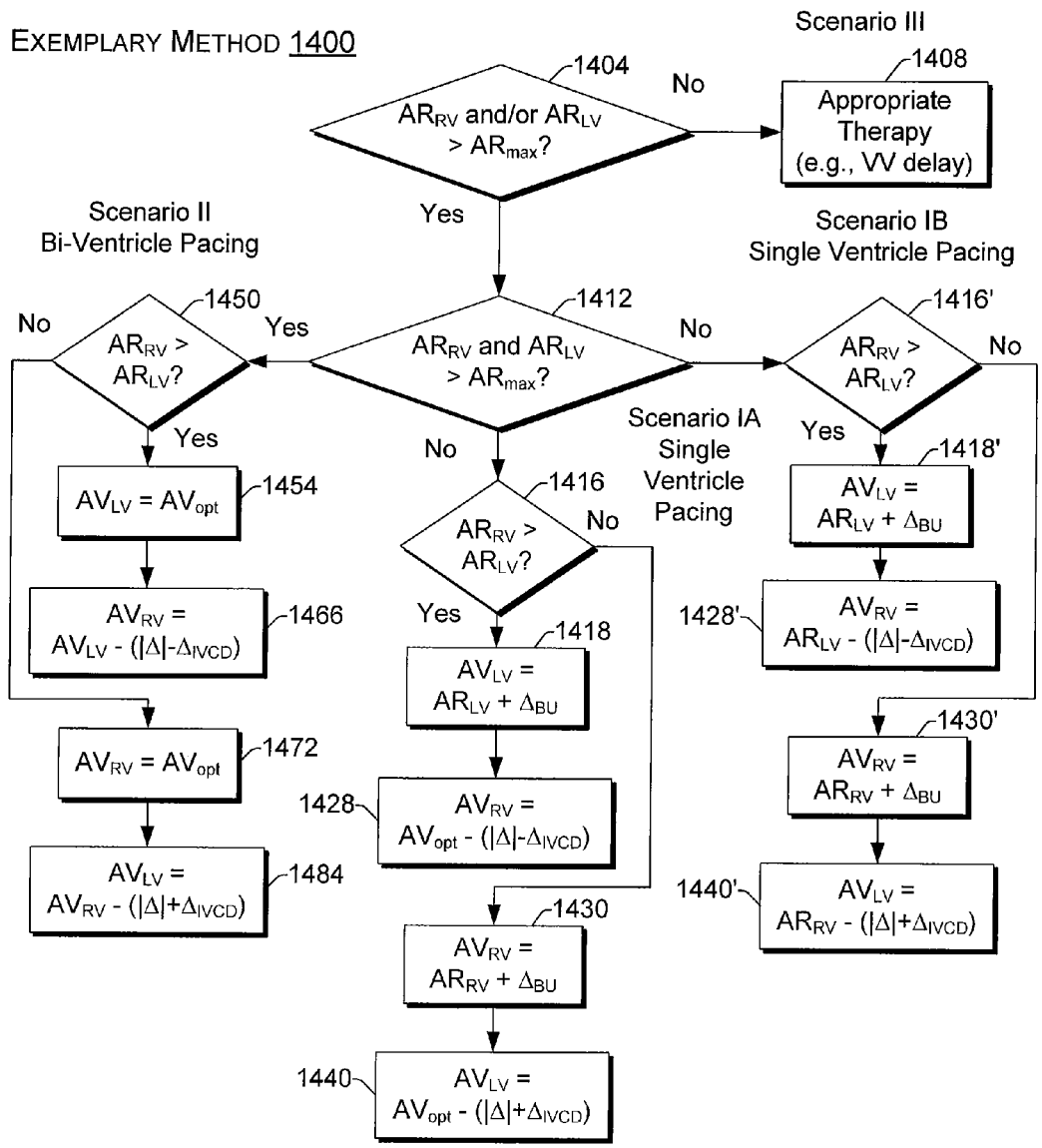
FIG. 14 is a block diagram of an exemplary method for ventricular pacing with scenarios for pacing a single ventricle and a scenario for pacing both ventricles.

Various examples discuss CRT parameter optimization and, for such optimization, any of a variety of techniques may be used. FIGS. 13-15 show various aspects of CRT parameter optimization techniques.

Various delays or parameters discussed herein include:

| | |
|---|---|
| PP, AA | Interval between successive atrial events |
| PV | Delay between an atrial event and a paced ventricular event |
| $PV_{optimal}$ | Optimal PV delay |
| $PV_{RV}$ | PV delay for right ventricle |
| $PV_{LV}$ | PV delay for left ventricle |
| AV | Delay for a paced atrial event and a paced ventricular event |
| $AV_{optimal}$ | Optimal AV delay |
| $AV_{RV}$ | AV delay for right ventricle |
| $AV_{LV}$ | AV delay for left ventricle |
| $\Delta$ | Estimated interventricular delay, e.g., via IEGM, etc. |
| $\Delta_{programmed}$ | Programmed interventricular delay |
| $\Delta_{optimal}$ | (e.g., a programmed VV delay) Optimal interventricular delay, e.g., via hemodynamic sensing/sensor or other cardiac sensing |
| IVCD-RL | Delay between an RV event and a consequent sensed LV event |
| IVCD-LR | Delay between an LV event and a consequent sensed RV event |
| $\Delta_{IVCD}$ | Interventricular conduction delay |
| $\Delta P, \Delta A$ | Width of an atrial event |
| DD, AD | Interval between end of an atrial wave (e.g., P or A wave) and beginning of a R or QRS complex or other appropriate point |
| $\Delta DD, \Delta AD$ | $DD_{LV}\text{-}DD_{RV}$ or $AD_{LV}\text{-}AD_{RV}$ |

FIG. 13 shows an exemplary method 1300 for ventricular pacing. In a determination block 1304, an implantable device determines an $AR_{RV}$ time and an $AR_{RV}$ time or equivalent times wherein one or both rely on detection of an intrinsic atrial event. A decision block 1308 follows wherein a decision is made as to whether $AR_{RV}$ is greater than $AR_{RV}$. If $AR_{RV}$ exceeds $AR_{RV}$, then in a set block 1312, the right ventricle is set to the master and the left ventricle is set to the slave. If $AR_{RV}$ exceeds $AR_{RV}$, then in a set block 1316, the left ventricle is set to the master and the right ventricle is set to the slave. Both set blocks 1312, 1316 continue in a determination block 1320 which determines a $\Delta$ value based on the $AR_{RV}$ and $AR_{LV}$ times. A pace master block 1324 follows wherein the master ventricle is paced based on the $\Delta$ and a desired AV delay. The desired AV delay may be determined, for example, based on an echocardiogram or other study. The AV delay is optionally determined by an implantable device based on sensed information. Various techniques described further below use sensed information such as width of a P wave ($\Delta P$) or width of an A wave ($\Delta A$).

Thus, as described with respect to FIG. 13, such an exemplary method includes determining an atrial to ventricular activation time for a right ventricle, determining an atrial to ventricular activation time for a left ventricle, and determining a pacing sequence that paces the right ventricle prior to activation of the left ventricle if the time for the right ventricle exceeds the time for the left ventricle or that paces the left ventricle prior to activation of the right ventricle if the time for the left ventricle exceeds the time for the right ventricle wherein pacing of the prior activated ventricle occurs based at least in part on a difference between the time for the right ventricle and the time for the left ventricle and a desired atrio-ventricular delay. In some instances, an inter-ventricular delay may be used instead of, or in addition, to one or more atrial to ventricular activation times.

FIG. 14 shows a block diagram of an exemplary method 1400. While the method 1400 pertains to atrial pacing, such a method may omit atrial pacing (e.g., rely on an intrinsic atrial activity, etc.) and/or include atrial pacing and intrinsic atrial activity, etc. (e.g., PR, AR, AV, and/or PV). The exemplary method 1400 includes Scenarios IA, IB, II and III. Other exemplary techniques are presented further below with respect to changes in activity, noting that activity-based techniques may be used for the method of FIG. 14.

In a decision block 1404 a decision is made as to whether $AR_{RV}$ and/or $AR_{LV}$ have exceeded a predetermined $AR_{max}$ value. If neither value exceeds $AR_{max}$, then Scenario III follows, which may disable ventricular pacing or take other appropriate therapy per block 1408. Other appropriate therapy optionally includes therapy that achieves a desirable VV delay by any of a variety of techniques. If however one or both values exceed $AR_{max}$, then the method 1400 continues in another decision block 1412. The decision block 1412 decides whether $AR_{RV}$ and $AR_{LV}$ have exceeded $AR_{max}$. If both values do not exceed $AR_{max}$, then single ventricular pacing occurs, for example, per Scenario IA or Scenario IB. If both values exceed $AR_{max}$, then bi-ventricular pacing occurs, for example, Scenario II.

Scenario IA commences with a decision block 1416 that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{RV}$, then single ventricular pacing occurs in the left ventricle (e.g., left ventricle master).

For right ventricular pacing per Scenario IA, the method 1400 continues in a back-up pacing block 1418 where $AV_{LV}$ is set to $AR_{LV}$ plus some back-up time (e.g., $\Delta_{BU}$). The block 1418, while optional, acts to ensure that pacing will occur in the left ventricle if no activity occurs within some given interval. The method 1400 then continues in a set block 1428 where the parameter $\Delta_{IVCD}$ is used as a correction factor to set the $AV_{RV}$ delay to $AV_{optimal}-(|\Delta|-\Delta_{IVCD})$.

For left ventricular pacing per the Scenario IA, the method 1400 continues in a back-up pacing block 1430 where $AV_{RV}$ is set to $AR_{RV}$ plus some back-up time (e.g., $\Delta_{BU}$). The block 1430, while optional, acts to ensure that pacing will occur in the left ventricle if no activity occurs within some given interval. The method 1400 then continues in a set block 1440 where the parameter $\Delta_{IVCD}$) is used as a correction factor to set the $AV_{LV}$ delay to $AV_{optimal}-(|\Delta|+\Delta_{IVCD})$.

Scenario IB commences with a decision block 1416' that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing per Scenario IB, the method 1400 continues in a back-up pacing block 1418' where $AV_{LV}$ is set to $AR_{LV}$ plus some back-up time (e.g., $\Delta_{BU}$). The block 1418', while optional, acts to ensure that pacing will occur in the left ventricle if no activity occurs within some given interval. The method 1400 then continues in a set block 1428' where the parameter $\Delta_{IVCD}$ is used as a correction factor to set the $AV_{RV}$ delay to $AR_{LV}-(|\Delta|-\Delta_{IVCD})$. Hence, in this example, a pre-determined $AV_{optimal}$ is not necessary.

For left ventricular pacing per the Scenario IB, the method 1400 continues in a back-up pacing block 1430' where $AV_{RV}$ is set to $AR_{RV}$ plus some back-up time (e.g., $\Delta_{BU}$). The block 1430', while optional, acts to ensure that pacing will occur in the left ventricle if no activity occurs within some given interval. The method 1400 then continues in a set block 1440' where the parameter $\Delta_{IVCD}$ is used as a correction factor to set the $AV_{LV}$ delay to $AR_{RV}+\Delta_{IVCD}$). Again, in this example, a pre-determined $AV_{optimal}$ is not necessary.

Referring again to the decision block 1412, if this block decides that bi-ventricular pacing is appropriate, for example, Scenario II, then the method 1400 continues in a decision block 1450, which that decides if $AR_{RV}$ is greater than $AR_{LV}$. If $AR_{RV}$ exceeds $AR_{LV}$, then bi-ventricular pacing occurs wherein the right ventricle is the master (e.g., paced prior to the left ventricle or sometimes referred to as left ventricle slave). If $AR_{RV}$ does not exceed $AR_{LV}$, then bi-ventricular pacing occurs wherein the left ventricle is the master (e.g., paced prior to the right ventricle or sometimes referred to as right ventricle slave).

For right ventricular master pacing, the method 1400 continues in a set block 1454 which sets $AV_{LV}$ to $AV_{optimal}$. The method 1400 then uses $\Delta_{IVCD}$ as a correction factor in a set block 1466, which sets $AV_{RV}$ delay to $AV_{LV}-(|\Delta|-\Delta_{IVCD})$.

For left ventricular master pacing, the method 1400 continues in a set block 1472 which sets $AV_{RV}$ to $AV_{optimal}$. The method 1400 then uses $\Delta_{IVCD}$ as a correction factor in a set block 1484, which sets $AV_{LV}$ delay to $AV_{RV}-(|\Delta|+\Delta_{IVCD})$.

A comparison between $\Delta$ and $\Delta_{programmed}$ or $\Delta_{optimal}$ can indicate a difference between a current cardiac therapy or state and a potentially better cardiac therapy or state. For example, consider the following equation:

$$\alpha = \Delta_{optimal}/\Delta$$

where $\alpha$ is an optimization parameter. Various echocardiogram studies indicate that the parameter $\alpha$ is typically about 0.5. The use of such an optimization parameter is optional. The parameter $\alpha$ may be used as follows:

$$AV_{RV}=AV_{optimal}-\alpha|\Delta| \text{ or } PV_{RV}=PV_{optimal}\alpha|\Delta|$$

$$AV_{LV}=AV_{optimal}\alpha(|\Delta|+\Delta_{IVCD}) \text{ or}$$

$$PV_{LV}=PV_{optimal}\alpha(|\alpha|+\Delta_{IVCD})$$

If a parameter such as the aforementioned a parameter is available, then such a parameter is optionally used to further adjust and/or set one or more delays, as appropriate.

Various exemplary methods, devices, systems, etc., may consider instances where normal atrio-ventricular conduction exists for one ventricle. For example, if an atrio-ventricular conduction time for the right ventricle does not exceed one or more limits representative of normal conduction, then the atrio-ventricular time for the right ventricle may serve as a basis for determining an appropriate time for delivery of stimulation to the left ventricle (or vice versa). The following equation may be used in such a situation:

$$AV_{LV}=AR_{RV}-|\Delta| \text{ or } PV_{LV}=PR_{RV}-|\Delta|$$

This equation is similar to the equation used in blocks 1428' and 1440' of Scenario IB of FIG. 14. With respect to backup pulses, a backup pulse (e.g., for purposes of safety, etc.) may be set according to the following equation:

$$AV_{RV}=AR_{RV}+|\gamma| \text{ or } PV_{RV}=PR_{RV}+|\gamma|$$

Of course, administration of a backup pulse may occur upon one or more conditions, for example, failure to detect activity in the particular ventricle within a given period of time. In the foregoing equation, the parameter $\gamma$ is a short time delay, for example, of approximately 5 ms to approximately 10 ms. This equation is similar to the equation used in blocks 1418' and 1430' of FIG. 14.

In many instances, heart condition will affect $AR_{RV}$ and $AR_{LV}$, and IVCD (e.g., IVCD-RL and/or IVCD-LR), which, in turn, may affect an existing optimal VV delay setting. Various exemplary methods, devices, systems, etc., include triggering of an algorithm to update an existing optimal VV delay according to a predetermined time or event period or activity sensors for exercise, resting, etc. An exemplary device may include a learning method that learns based on differences in conduction times (e.g., $AR_{RV}$ and $AR_{LV}$, IVCD, etc.) such that parameters associated with different heart demands can be stored. The exemplary learning method may then extract such learned or other parameters to set an optimal VV delay.

In the aforementioned learning example, if the device learns on the basis of different cardiac demands, the device may adjust AV delay and/or VV delay and/or learn a new AV delay and/or VV delay upon a change in cardiac demand. According to this example, use of external measurement or sensing equipment (e.g., echocardiogram, etc.) is optional.

Further, use of internal measurement or sensing equipment for sensing pressure or other indicators of hemodynamic performance is optional. Again, adjustment and learning may rely on IEGM information and/or cardiac other rhythm information.

An exemplary method relies on an atrial to right ventricular conduction time, an atrial to left ventricular conduction time and a α parameter, for example, as described above, to determine an optimal AV delay and/or VV delay. Another exemplary method relies on an atrial to right ventricular conduction time, an atrial to left ventricular conduction time and a limit that may be used to decide whether one or more of the conduction times are acceptable. In these examples, an interventricular conduction time may be used in lieu of an atrial to ventricular conduction time, for example, where ventricular activity originates with a common atrial event.

According to various exemplary methods, devices, systems, etc., information acquired (e.g., sensed, detected and/or determined) may be used to diagnose cardiac condition. For example, an exemplary method may track AV delays and/or VV delays over time. Such information may then be used to determine subsequent therapy.

Various exemplary methods, devices, systems, etc., include determining an optimal interventricular delay (e.g., $\alpha_{optimal}$) using a modality such as an echocardiogram. While an internal echocardiogram or implantable hemodynamic sensors may be available or become available and be able to measure such optimal delays for a variety of patient circumstances (e.g., sleep, exercise, etc.), an exemplary method, device, system, etc., includes use of one or more internal sensors to measure and/or update such an optimal delay and/or to determine values for one or more parameters related to an optimal delay. For example, a blood pressure sensor (e.g., aortic arch, left atrium, etc.) may be used to determine or to update an optimal delay. Further, information may be collected over a period of time to determine heart condition (e.g., deterioration, improvement, etc.).

In general, an optimal interventricular delay will change as demand and/or heart conditions change. Thus, an exemplary method may determine an optimal interventricular delay during sleep on a nightly, a weekly or some other basis. Such an exemplary method may determine an optimal interventricular delay within a matter of minutes (e.g., approximately 5 heart beats). Such an exemplary method may be triggered according to a change in heart rate or some other parameter related to heart condition. Over time or at time of programming, an exemplary device may store one or more optimal interventricular delays as a function of heart rate, heart condition, etc., and then implement a selected delay from the stored delays upon occurrence of a rate, condition, etc., or a change in rate, condition, etc. Such dynamic control of interventricular delay can improve cardiac performance and potentially allow for an improvement in patient quality of life (e.g., allow for a broader range of patient activity). If after some predetermined period of time or upon occurrence of a particular condition, an exemplary device may indicate a need for a more rigorous determination, for example, via an echocardiogram.

As described herein, various techniques include adjusting one or more pacing parameters based at least in part on patient activity. Such techniques may use variables such as ΔP, ΔA, DD and/or AD. Two parameters, δ and β, are discussed in more detail below. The parameter δ may depend on ΔP or ΔA while the parameter β may depend on δ and DD or AD, as indicated by the following equations:

$$\delta = f(\Delta P) \text{ or } f(\Delta A)$$

$$\beta = \delta / DD \text{ or } \delta / AD$$

These parameters may be used to determine one or more pacing parameters, for example, as indicated by the following equations:

$$PV = \Delta P + \beta * DD$$

$$AV = \Delta A + \beta * AD$$

Variations of these four foregoing equations are presented with respect to FIG. 15. The PV or AV forms may be used to determine an optimal PV or AV. For example, $AV_{opt}$ may be determined and then used in any of the various scenarios of FIG. 14. For VV delay, techniques described above may be used. However, as discussed in more detail below, VV may depend on activity and hence may change when activity state changes. VV is used for bi-ventricular pacing and the following equations may be used:

$$PV'' = PV' + VV$$

$$AV'' = AV' + VV$$

where PV' and AV' are for the master ventricle and where PV'' and AV'' are for the slave ventricle.

Various exemplary method discussed herein include sensing patient activity, for example, using an activity sensor (e.g., accelerometer, minute ventilation, etc.), and adjusting one or more pacing parameters based at least in part on such sensing. An exemplary method may select a pacing parameter for a pacing therapy based on patient activity state. For example, an implantable device may include a set of parameters for a rest state and a set of parameters for an exercise state.

An exemplary method may include monitoring one or more characteristics of atrial activity and adjusting one or more pacing parameters based at least in part on such monitoring. For example, a method may include monitoring P wave width (e.g., ΔP) and using P wave width to adjust one or more pacing parameters whereas another method may include monitoring A wave width (e.g., ΔA) and using A wave width to adjust one or more pacing parameters. P wave width or A wave width may increase as patient activity increases. Thus, if the P wave width or the A wave width exceed a limit, then an exemplary method may call for a change in one or more pacing parameters.

An exemplary method may include disabling ventricular pacing and measuring DD interval or AD interval, respectively, and adjusting one or more pacing parameters based at least in part on such measuring. DD interval or AD interval may increase as patient activity increases. Thus, if the DD interval (e.g., $DD_{RV}$ or $DD_{LV}$) or the AD interval (e.g., $AD_{RV}$ or $AD_{LV}$ exceed a limit, then an exemplary method may call for a change in one or more pacing parameters.

An exemplary method may include sensing PP interval as a surrogate for patient activity and adjusting one or more pacing parameters based at least in part on such sensing. In general, PP interval will decrease as patient activity increases; noting that certain conditions or drugs may make this technique less useful (e.g., beta blockers, high NYHA class, etc.). While PP interval is mentioned, other intervals may be used based on a marker that occurs once per cardiac cycle (e.g., $R_{RV}$, $R_{LV}$, etc.). An exemplary method may select a pacing parameter for a pacing therapy based on an interval. For example, an implantable device may include a set of parameters for a long interval (e.g., a rest state) and a set of parameters for a short interval (e.g., an exercise state).

While the foregoing discussion pertains to schemes individually, an exemplary method may use any of the various schemes, as appropriate. For example, an exemplary method may include monitoring P wave width and disabling ventricular pacing to measure DD interval based at least in part on P wave width.

FIG. 15 shows various exemplary methods 1500. While equations are presented, implementation of techniques described herein may be implemented using any of a variety of forms of control logic. For example, look-up tables may be used together with logic that stores and/or pulls data from the look-up table. Control logic to achieve the overall goals achieved by the various equations 1500 may be achieved by control logic that does not explicitly rely on the equations, as presented.

A state block 1510 defines various activity states. The activity states include a base state, for example, a rest state denoted by a subscript "0". In other examples, the subscript "rest" is used. The activity states include at least two states, for example, a base state and another activity state. In FIG. 15, the states range from the base state to activity state "N", which may be an integer without any numeric limitation (e.g., N may equal 5, 10, 100, 1000, etc.). The number of activity states may depend on patient condition and patient activity. For example, a patient that is bedridden may have few activity states when compared to a young patient (e.g., 40 years old) fitted with a pacemaker that leads an active life with a regular exercise regimen.

A PV or AV states block 1520 presents equations for the parameters β and δ as well as for a base state PV and AV and PV and AV for a state other than a base activity state, referred to as $AS_x$, where x=1, 2, ... N. In addition, sets of equations are presented that include a pacing latency term PL. Pacing latency is generally defined as the time between delivery of a cardiac stimulus and time of an evoked response caused by the stimulus. More specifically, an implantable device may use the time of delivery of a stimulus and the time at which a sensed, evoked response signal deviates from a baseline, which is referred to herein as $PL_I$ (e.g., to initiation of evoked response). Such a signal is usually sensed using the lead that delivered the stimulus, however, electrode configuration may differ (e.g., unipolar delivery and bipolar sensing, bipolar delivery and unipolar sensing, etc.). In some instances, the pacing latency may exceed 100 ms due to ischemia, scarring, infarct, etc. Thus, PV or AV timing may be adjusted accordingly to call for earlier delivery of a stimulus to a ventricle or ventricles.

An exemplary algorithm may determine PL for the right ventricle (for a right ventricular lead) and for the left ventricle (for a left ventricular lead) during measurement of IVCD-LR and IVCD-RL (e.g., parameters that may be used to determine VV). While pacing latency can be measured from the time of delivering a pacing pulse to the time of an evoked response at the pacing lead ($PL_I$), pacing latency may be measured alternatively from the time of the pulse to the peak of an evoked response ($PL_{Peak}$) In either instance, such techniques may shorten block and/or discharge periods, optionally to a minimum (e.g., about 3 ms in some commercial ICDs). An algorithm may also provide for detection of capture, for example, using an integral (e.g., PDI) and/or a derivative (e.g., $D_{max}$). In general, pacing latencies for LV and RV leads correspond to situations where capture occurs. In yet another alternative, during P wave and PR measurement, a time delay from a marker of a sensed R event to the peak of a QRS complex may be measured and used as a correction term akin to pacing latency.

A VV states block 1530 presents equations for the parameters α, Δ and $Δ_{IVCD}$ and VV for a base activity state ($AS_0$) and another activity state ($AS_x$). These equations may be used in various scenarios of the method 1400 of FIG. 14 or other methods (see, e.g., exemplary schemes of FIG. 4 and corresponding methods). Noting that some differences exist between the method 1400 and the equations of FIG. 15, for example, lack of absolute values for the parameter Δ. To account for this variation, the value of Δ is used to determine whether the right ventricle or left ventricle is paced for single ventricle pacing or is the master for bi-ventricular pacing. If the Δ is less than 0 ms, then the right ventricle is paced or the master whereas if Δ is greater than 0 ms, then the left ventricle is paced or the master. For bi-ventricular pacing, the PV or AV state equation is used for the master ventricle and then the VV equation is used to determine timing of the slave ventricle. Hence, the control logic uses Δ to determine whether the PV or AV state equation will correspond to the left ventricle or the right ventricle.

The block 1530 also includes equations for a pacing latency differential, referred to as ΔPL. This term may be calculated, for example, as the difference between $PL_{Peak}$ and a generic or average pacing latency (e.g., $PL_{Ave}$ based on a sampling of "normal" pacing latencies). Hence, ΔPL may represent a difference from a normal pacing latency. A normal pacing latency may be around 70 ms and hence APL may equal $PL_{Peak}$ minus 70 ms. The parameter ΔPL may be calculated for both the right ventricle (e.g., ΔPL-RV) and the left ventricle (e.g., ΔPL-LV). Where VV has positive sign that indicates to pace LV first, then the correction term ΔPL-LV may be added while where VV has a negative sign that indicates to pace RV first then the correction term ΔPL-RV may be added. In block 1230, the term APL is shown without indication of LV or RV, noting that use of ΔPL-LV or ΔPL-RV may be determined accordingly. A criterion or criteria may be used to decide if a pacing latency correction term should be used in determining PV, AV or VV. For example, if PL exceeds a certain limit, then a pacing latency correction term or terms may be used. Similarly, if APL exceeds a certain limit, then a pacing latency correction term or terms may be used.

Recent clinical data indicates that during exercise, optimal PV/AV delays are prolonged compared with those at rest in HF patients. Various exemplary techniques described herein can account for changes for HF patients during exercise and at rest through the duration of P wave or A wave and an appropriate atrio-ventricular conduction delay. During exercise some HF patients may have an increase in width of atrial signals or atrio-ventricular conduction delays or both that would lead to prolonged optimal AV and PV delays. In patients with normal rate responses, AV or PV delays may have negative hysteresis or remain the same as at rest.

While various examples mention use of a "rest" state, a rest state may be a base state. Alternatively, a base state may be a state other than a rest state. For example, a base state may correspond to a low activity state where a patient performs certain low energy movements (e.g., slow walking, swaying, etc.) that may be encountered regularly throughout a patient's day. Thus, a base state may be selected as a commonly encountered state in a patient's waking day, which may act to minimize adjustments to PV, AV or VV. Further, upon entering a sleep state, a device may turn off adjustments to PV, AV or VV and assume sleep state values for PV, AV or VV. Such decisions may be made according to a timer, a schedule, an activity sensor, etc.

An exemplary computing device may include control logic to assess cardiac condition based at least in part on information acquired from an implantable device where the information includes, for example, one or more CRT parameter and/or one or more rate adaptive pacing parameters or combinations thereof (e.g., α, Δ, IVCD-RL, IVCD-LR, $\Delta_{IVCD}$, AV, PV, VV, response time, recovery time, $Th_{ID}$, $Th_{AD}$, $Slope_{R/A}$, etc.). The computing device may be the implantable device, or in other words, an implantable device may be capable of assessing patient condition and more particularly cardiac condition.

Various exemplary methods may be implementable wholly or to varying extent using one or more computer-readable media that include processor executable instructions for performing one or more actions. For example, the device 100 of FIG. 2 shows various modules associated with a processor 220. Hence, a module may be developed using an algorithm described herein. Such a module may be downloadable to an implantable device using a device programmer or may be incorporated into a device during manufacture by any of a variety of techniques. At times such instructions are referred to as control logic.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method implemented by an implantable cardiac resynchronization therapy device, the method comprising:
   delivering a cardiac resynchronization therapy that comprises an atrio-ventricular delay and an interventricular delay;
   monitoring patient activity level;
   optimizing the atrio-ventricular delay and the interventricular delay for a plurality of patient activity levels including a rest state to generate a plurality of optimal atrio-ventricular delays and a plurality of optimal interventricular delays, each atrio-ventricular delay and each interventricular delay corresponding to a unique activity level;
   storing the optimal atrio-ventricular delays and the optimal interventricular delays in association with the corresponding patient activity levels;
   detecting a change in patient activity level including a change to the rest state;
   adjusting an atrial pacing rate in response to the detected change in patient activity level based at least in part on a heart failure status; and
   automatically adjusting the atrio-ventricular delay and the interventricular delay, in response to the detected change in patient activity level including to the rest state, wherein the adjusting comprises using a stored optimal atrio-ventricular delay that corresponds to the patient activity level and a stored optimal interventricular delay that corresponds to the patient activity level.

2. The method of claim 1 wherein the monitoring comprises monitoring intrinsic heart rate.

3. The method of claim 1 wherein the monitoring comprises acquiring information from an accelerometer.

4. The method of claim 1 wherein the monitoring comprises determining minute ventilation.

5. The method of claim 1 wherein the heart failure status comprises a NYHA class.

6. The method of claim 1 wherein the detected change in patient activity comprises an increase in patient activity and wherein the adjusting an atrial pacing rate comprises adjusting the atrial pacing rate incrementally to a maximum sensor rate.

7. The method of claim 6 wherein the adjusting comprises adjusting the atrial pacing rate incrementally over a response time.

8. The method of claim 7 wherein the response time comprises a pre-determined response time.

9. The method of claim 1 wherein the detected change in patient activity comprises a decrease in patient activity and wherein the adjusting an atrial pacing rate comprises adjusting the atrial pacing rate decrementally to a patient intrinsic heart rate or a base rate.

10. The method of claim 9 wherein the adjusting comprises adjusting the atrial pacing rate decrementally over a recovery time.

11. The method of claim 10 wherein the recovery time comprises a pre-determined recovery time.

12. The method of claim 10 wherein the recovery time depends on an intrinsic heart rate.

13. The method of claim 1 wherein the detecting a change in patient activity comprises detecting a change from a rest state to an active state.

14. The method of claim 13 wherein the setting the atrio-ventricular delay and the interventricular delay sets the atrio-ventricular delay to an active state value and sets the interventricular delay to an active state value.

15. The method of claim 1 wherein the detecting a change in patient activity comprises detecting a change from an active state to a rest state.

16. The method of claim 15 wherein the setting the atrio-ventricular delay and the interventricular delay sets the atrio-ventricular delay to a rest state value and sets the interventricular delay to a rest state value.

17. An implantable cardiac resynchronization therapy device comprising:
   means for delivering cardiac resynchronization therapy that comprises an atrio-ventricular delay and an interventricular delay;
   means for monitoring patient activity level;
   means for optimizing the atrio-ventricular delay and the interventricular delay for a plurality of patient activity levels including a rest state to generate a plurality of optimal atrio-ventricular delays and a plurality of optimal interventricular delays, each atrio-ventricular delay and each interventricular delay corresponding to a unique activity level;
   means for detecting a change in patient activity level including a change to the rest state; and
   means for automatically adjusting the atrio-ventricular delay and the interventricular delay, in response to the detected change in patient activity level including to the rest state, wherein the adjusting comprises using a stored optimal atrio-ventricular delay that corresponds to the patient activity level and a stored optimal interventricular delay that corresponds to the patient activity level.

18. An implantable cardiac resynchronization therapy device comprising:
   circuitry configured to control delivery of stimulation to a patient's heart according to an atrio-ventricular delay and an interventricular delay;
   a sensor configured to monitor patient activity levels; and
   wherein the circuitry is configured to optimize the atrio-ventricular delay and the interventricular delay for a plurality of patient activity levels including a rest state to generate a plurality of optimal atrio-ventricular delays and a plurality of optimal interventricular delays, wherein each atrio-ventricular delay and each interventricular delay corresponds to a unique activity level, and wherein the circuitry is further configured to receive information from the sensor to determine a patient activity level including a change to the rest state, and to automatically adjust the atrio-ventricular delay and the interventricular delay based on a change in the patient activity level including to the rest state.

* * * * *